(12) United States Patent
Schibli et al.

(10) Patent No.: US 10,617,879 B2
(45) Date of Patent: Apr. 14, 2020

(54) WIRELESS CARDIAC PACEMAKER WITH CERMET ELECTRODE

(71) Applicant: HERAEUS DEUTSCHLAND GMBH & CO. KG, Hanau (DE)

(72) Inventors: Stefan Schibli, Frankfurt (DE); Jens Trötzschel, Ronneburg (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 468 days.

(21) Appl. No.: 15/322,439

(22) PCT Filed: Jun. 26, 2015

(86) PCT No.: PCT/EP2015/064493
§ 371 (c)(1),
(2) Date: Dec. 27, 2016

(87) PCT Pub. No.: WO2015/197810
PCT Pub. Date: Dec. 30, 2015

(65) Prior Publication Data
US 2017/0136245 A1    May 18, 2017

(30) Foreign Application Priority Data
Jun. 27, 2014 (DE) .......... 10 2014 009 322

(51) Int. Cl.
*A61N 1/37* (2006.01)
*A61N 1/375* (2006.01)
(Continued)

(52) U.S. Cl.
CPC ........... *A61N 1/3756* (2013.01); *A61N 1/05* (2013.01); *A61N 1/362* (2013.01); *A61N 1/3754* (2013.01); *A61N 1/04* (2013.01); *A61N 1/36* (2013.01)

(58) Field of Classification Search
CPC ........ A61N 1/3756; A61N 1/362; A61N 1/05; A61N 1/3754; A61N 1/36; A61N 1/04
See application file for complete search history.

(56) References Cited

U.S. PATENT DOCUMENTS 8,000,804 B1    8/2011  Wessendorf et al.
2004/0059392 A1*  3/2004  Parramon ............ A61N 1/3605
                                                   607/36
(Continued)

FOREIGN PATENT DOCUMENTS

EP    1714670    10/2006

OTHER PUBLICATIONS

International Search Report and Written Opinion for International Application No. PCT/EP2015/064493 dated Oct. 14, 2015 (7 pages).

*Primary Examiner* — Rex R Holmes
(74) *Attorney, Agent, or Firm* — Dicke, Billig & Czaja, PLLC

(57) ABSTRACT

One aspect relates to a device including a hollow body, an inner volume and a surrounding volume. The inner volume includes an electronic component and the hollow body encloses the inner volume and includes a first component, a second component and an electrode. The first component is electrically conductive and the second component electrically insulates the electrode from the first component. The electrode includes a cermet, connects the inner volume to the surrounding volume in an electrically conductive manner, and includes a contact surface. The contact surface contacts eukaryotic tissue and has a maximum distance from the electronic component of less than 80 mm.

15 Claims, 9 Drawing Sheets

(51) Int. Cl.
*A61N 1/05* (2006.01)
*A61N 1/362* (2006.01)
*A61N 1/04* (2006.01)
*A61N 1/36* (2006.01)

(56) References Cited

U.S. PATENT DOCUMENTS

| | | |
|---|---|---|
| 2007/0156180 A1* | 7/2007 | Jaax .................. A61M 5/14276 |
| | | 607/2 |
| 2011/0034965 A1 | 2/2011 | Troetzschel et al. |
| 2012/0193118 A1* | 8/2012 | Kempf .................. A61N 1/3754 |
| | | 174/50.53 |
| 2012/0193119 A1 | 8/2012 | Kempf et al. |
| 2012/0194981 A1 | 8/2012 | Kempf et al. |
| 2013/0338750 A1 | 12/2013 | Eck et al. |

* cited by examiner

100

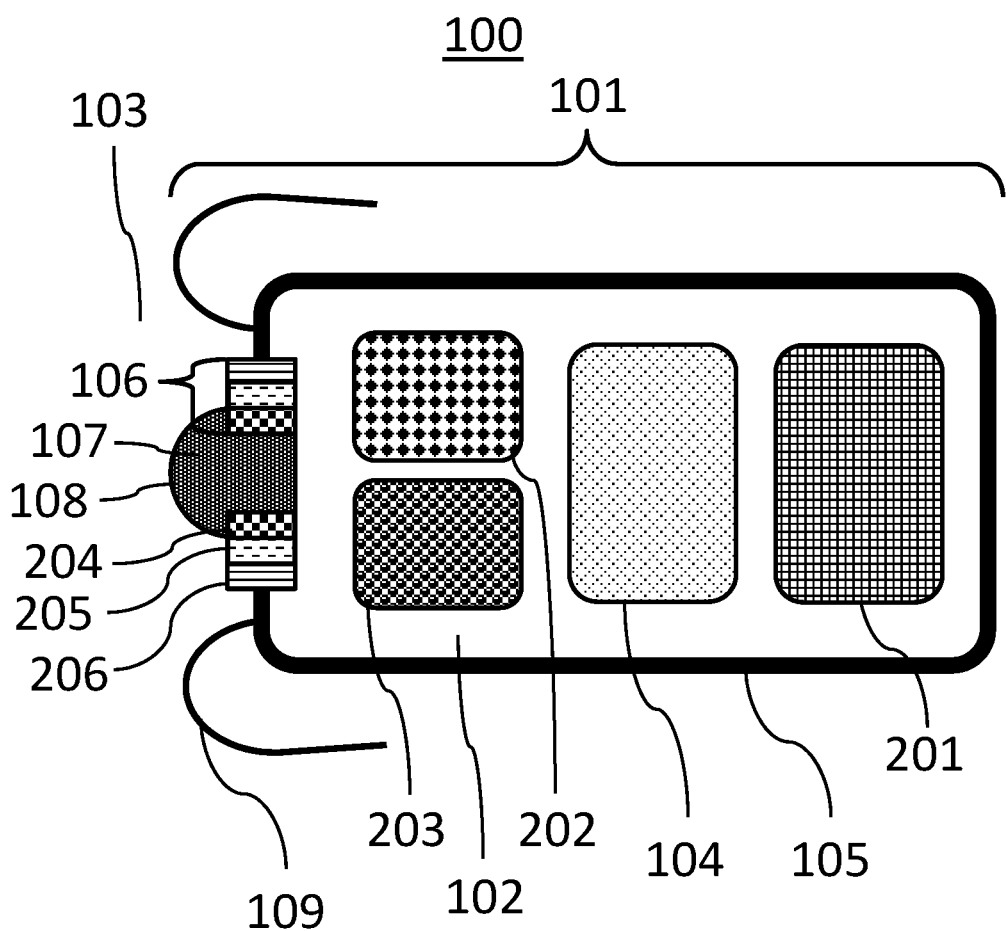
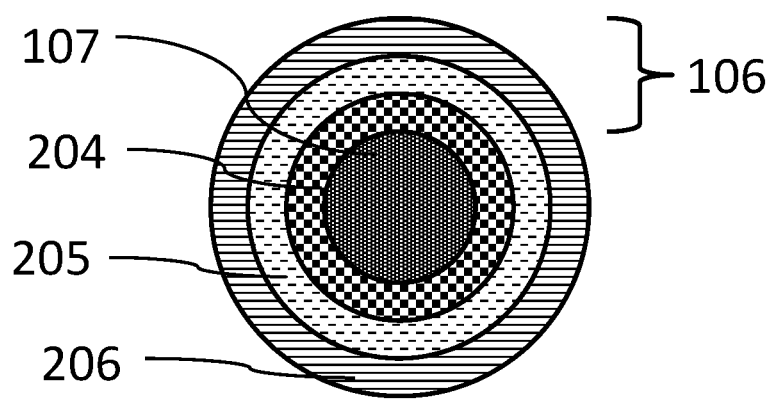

100

100

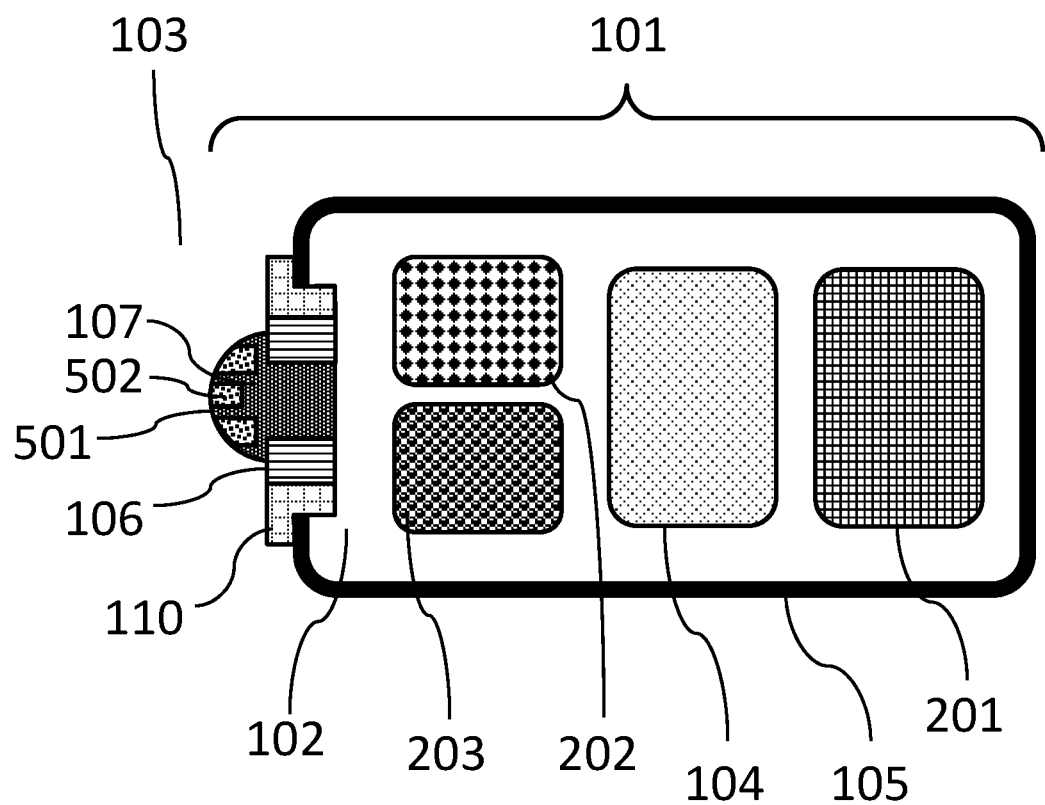

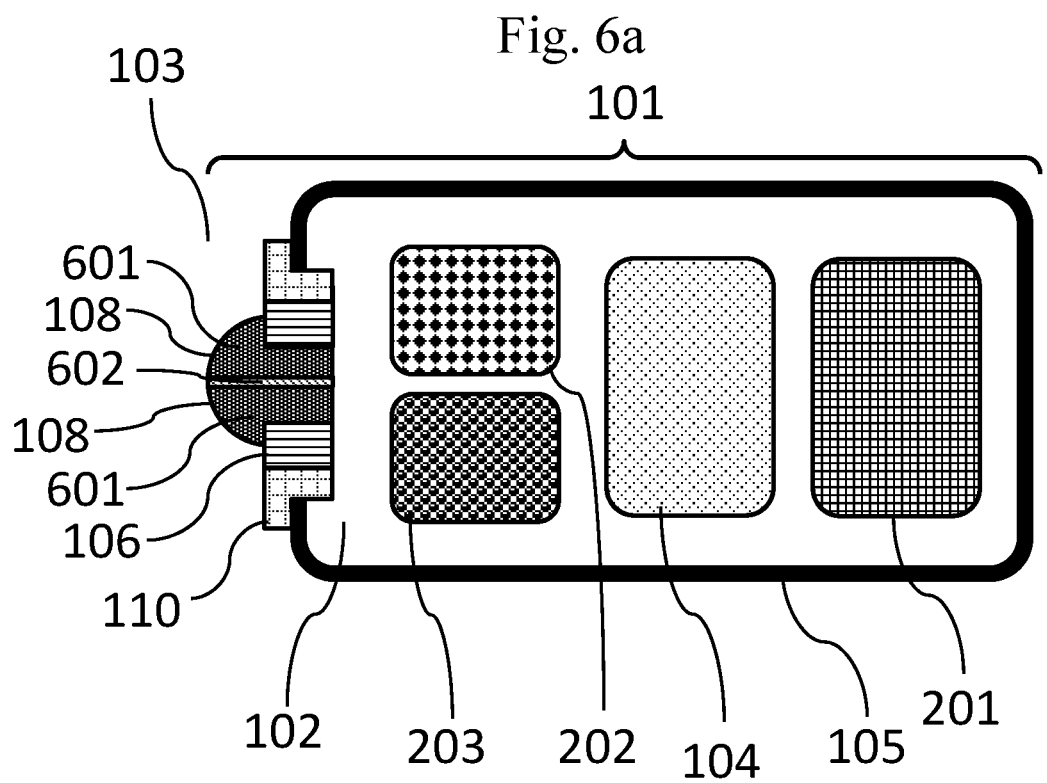
Fig. 6a
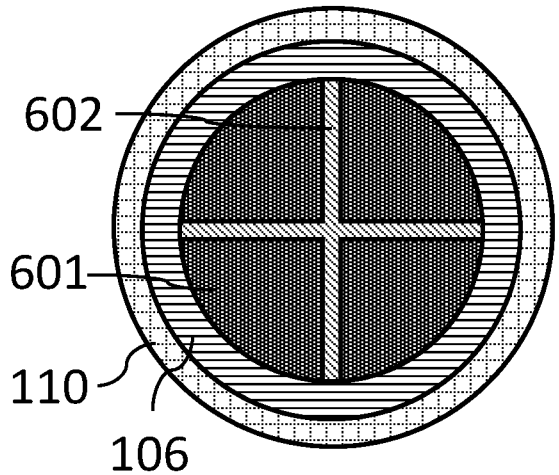 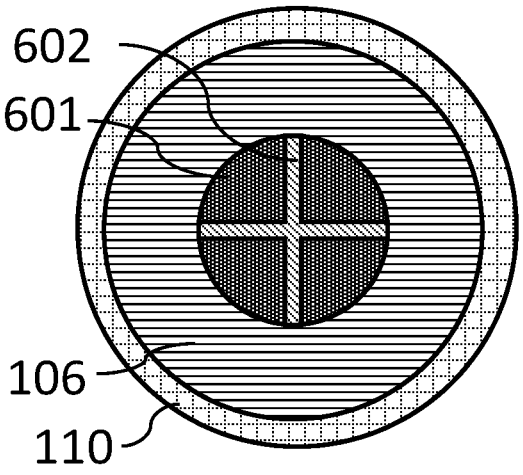
Fig. 6b  Fig. 6c

800

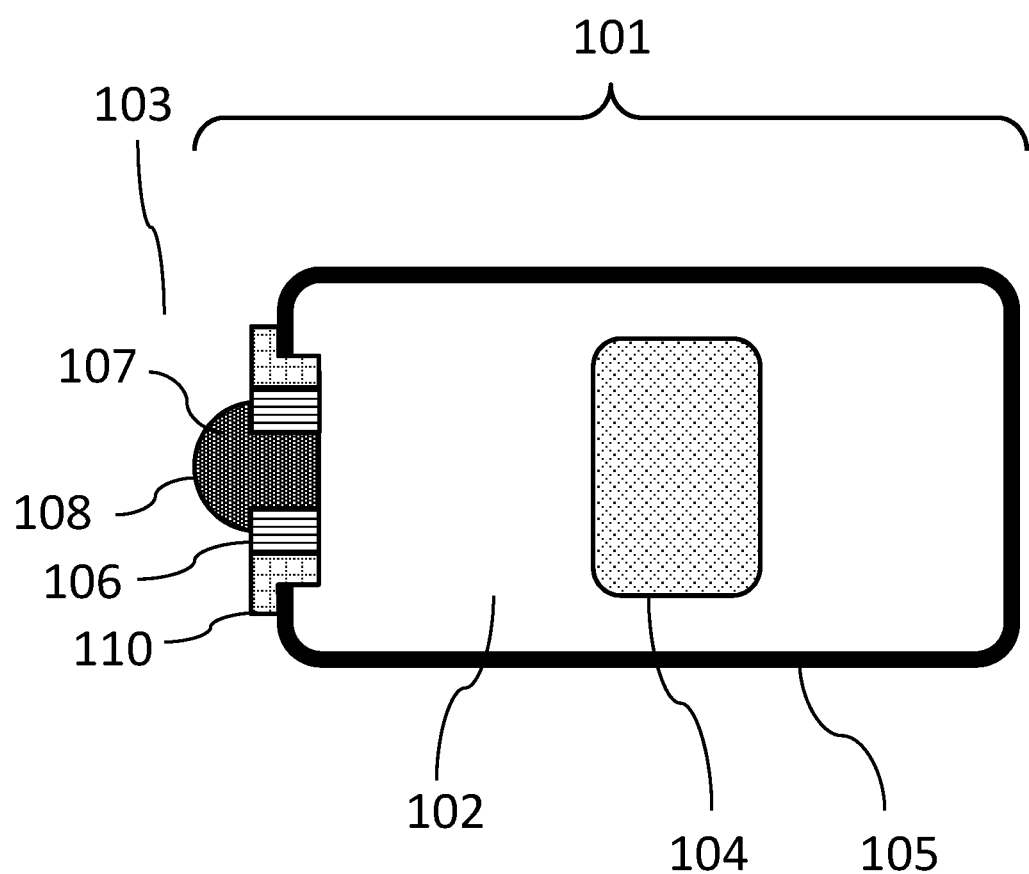

WIRELESS CARDIAC PACEMAKER WITH CERMET ELECTRODE

CROSS REFERENCE TO RELATED APPLICATION

This Utility patent application claims the benefit of the filing date of German Application No. DE 10 2014 009 322.0, filed Jun. 27, 2014, and International Application No. PCT/EP2015/064493, filed Jun. 26, 2015, both of which are herein incorporated by reference.

BACKGROUND

One aspect relates to a device comprising a hollow body, an inner volume and a surrounding volume, wherein the hollow body comprises a cermet electrode; to a method for producing a device, comprising the method step of connecting a housing to a cermet electrode; a device obtainable by a method comprising the method step of connecting a housing to a cermet electrode; and to a use of a cermet electrode for producing a wireless cardiac pacemaker.

Electrical stimulation of human or animal tissue for therapeutic purposes has long been known in the art. For therapy of this kind, a device providing electrical pulses can be implanted in a human or animal body to be treated. Examples of implantable devices that provide electrical pulses are pacemakers and defibrillators. Pacemakers known in the prior art are bladder pacemakers, diaphragm pacemakers, intestinal pacemakers, respiratory pacemakers, brain pacemakers and cardiac pacemakers. Implantable cardiac pacemakers that have long been known in the art typically comprise a control unit, which is connected to a measuring unit and to an electrical pulse generator. The measuring unit detects electrical potentials of the heart via attached electrodes. The electrical pulse generator delivers electrical stimulation pulses to cardiac muscle tissue via attached electrodes. Conventional cardiac pacemakers that have long been known in the art are implanted at some distance from the heart, for example below the collarbone in humans. From the measuring unit contained in the housing and from the electrical pulse generator, flexible electrode lines are routed into a heart chamber. There, the electrode lines end at electrodes which transmit the electrical stimulation pulses to the cardiac muscle tissue. The control unit is powered via a likewise implanted battery. The likewise implanted battery can be contained in the housing or can be connected to the latter by a plug-socket connection. Numerous refinements of such cardiac pacemakers concern the materials used, the programming of the control unit, and the power supply. Cardiac pacemakers presently known in the art do not comprise the flexible electrode lines between the measuring unit and electrodes and between the electrical pulse generator and electrodes. Instead, the housing is designed such that it comprises the electrodes on its outer sides. By suitable dimensioning of such a cardiac pacemaker, it can be implanted in a heart, where the electrodes are in contact with cardiac muscle tissue. Persons skilled in the art refer to cardiac pacemakers of this kind as wireless cardiac pacemakers. A wireless cardiac pacemaker of this kind is disclosed in EP 1 714 670 A1. A wireless cardiac pacemaker comprises at least two electrodes. One electrode is formed as a cathode, and a further electrode is formed as an anode. The cathode is often designed as a tip electrode and the anode as a ring electrode. The cathode serves to stimulate the cardiac muscle, and the anode serves to measure heart activity. The housing, which is made of titanium, is customarily used as the anode. The cathode is normally formed by a contact body and a feed-through wire. The contact body is designed to contact the tissue that is to be stimulated. The contact body is normally made of a platinum-iridium alloy and is produced by machining. The feed-through wire is welded onto the contact body and establishes an electrical connection between the electronics inside the housing and the contact body. As regards the implantability of the cardiac pacemaker, it is of great importance that the electrical feed-through is hermetically sealed. To achieve this, the feed-through wire normally runs through a ceramic ring, to which the feed-through wire is soldered by a gold solder. The ceramic ring in turn is soldered into a metal flange, which is flanged onto the housing by welding.

The wireless cardiac pacemakers of the prior art have at least the following disadvantages. An electrode consists of several parts, at least the contact body and the feed-through wire. These parts have to be connected in at least one work step. This work step makes a method for producing a wireless cardiac pacemaker of the prior art more expensive or more laborious, or both. An electrode of a wireless cardiac pacemaker of the prior art is constructed in several pieces. This increases the electrical resistance compared to a one-piece electrode, and this increases the power consumption of a wireless cardiac pacemaker of the prior art. The increased power consumption shortens the battery life of a wireless cardiac pacemaker of the prior art. This shortens the time between necessary surgical interventions in the organism in which the wireless cardiac pacemaker of the prior art is implanted. The connection between the parts of the electrode of the wireless cardiac pacemaker of the prior art may come loose, which can adversely affect the function of the wireless cardiac pacemaker or can damage the organism in which the wireless cardiac pacemaker is implanted. Moreover, the feed-through wire has to be connected to the ceramic ring in an additional work step. This work step too makes a method for producing a wireless cardiac pacemaker of the prior art more expensive or more laborious, or both. In the prior art, the connecting of the feed-through wire to the ceramic ring is effected by soldering with a gold solder. The use of the gold solder makes the method for producing a wireless cardiac pacemaker of the prior art more expensive. The connection of the ceramic ring to the feed-through wire of wireless cardiac pacemaker of the prior art may also come loose, which can adversely affect the function of the wireless cardiac pacemaker or can damage the organism in which the wireless cardiac pacemaker is implanted. Moreover, the connection of the ceramic ring to the feed-through wire is a potential source of leakage of the wireless cardiac pacemaker of the prior art. Furthermore, the production of a contact body of a wireless cardiac pacemaker of the prior art is laborious or expensive, or both. It is advantageous to minimize the outer (macroscopic) surface of the contact body which, for stimulation purposes, is brought into electrically conductive contact with the cardiac muscle tissue. On the other hand, the outer surface area of the contact body in mechanical contact with the cardiac muscle tissue should not be so small that the electrode perforates the cardiac muscle tissue. Accordingly, in the prior art, the surface of the contact body brought into contact with the cardiac muscle tissue is provided with a partially electrically insulating coating, for example with Parylene. Such coating adds a further work step to a method for producing a wireless cardiac pacemaker of the prior art. Such a work step makes a method for producing a wireless cardiac pacemaker of the prior art more expensive or more laborious, or both. Moreover, such a coating or parts of such a coating may come loose, which can adversely affect the function of the wireless cardiac pacemaker or can damage the organism in which the wireless cardiac pacemaker is implanted. Furthermore, if the inner (microscopic) surface of the contact body coming into contact with the cardiac muscle tissue is as large as possible, this affords advantages as regards operating a wireless cardiac pacemaker. In the prior art, this surface is therefore sintered or coated, or both. As regards a method for producing a wireless cardiac pacemaker, this adds further work steps that are laborious or expensive, or both. Moreover, such a coating or parts of such a coating may also come loose, which can adversely affect the function of the wireless cardiac pacemaker or can damage the organism in which the wireless cardiac pacemaker is implanted. In a wireless cardiac pacemaker of the prior art, the housing is used as the anode. It is advantageous to increase an inner (microscopic) surface of a part of the housing. In the prior art, this is done by sintering or coating, or both. As regards a method for producing a wireless cardiac pacemaker, this adds further work steps that are laborious or expensive, or both. Moreover, such a coating or parts of such a coating may also come loose, which can adversely affect the function of the wireless cardiac pacemaker or can damage the organism in which the wireless cardiac pacemaker is implanted. Moreover, the use of the housing as the anode makes it difficult to fix electronics in the housing without causing an electrical short circuit with the housing. Since the anode is the entire housing, a measurement of the heart activity is easily affected by interference signals. If electrical stimulation or a measurement of electrical potentials is to take place separately at different points of cardiac muscle tissue that lie close to each other, it is advantageous to arrange a plurality of electrodes close together. With electrodes of wireless cardiac pacemakers of the prior art, such an arrangement is impossible, or it is possible only at great expense. A fundamental problem when it comes to implanting wireless cardiac pacemakers is that of inflammation. Steroidal anti-inflammatories can be used to counter the occurrence of inflammation caused by the implanted wireless cardiac pacemaker. In the prior art, these anti-inflammatories are introduced into a bore in an electrode of the wireless cardiac pacemaker. A multiplicity of such bores containing steroidal anti-inflammatories would be advantageous. Producing a multiplicity of bores in an electrode of a wireless cardiac pacemaker of the prior art is very laborious.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2a illustrates a schematic cross section of a further embodiment of a device according to one embodiment, in a side view.

FIG. 2b illustrates a schematic view of the electrode and of the second component of the embodiment in FIG. 2a from the direction of the surrounding volume.

FIG. 5 illustrates a schematic cross section of a further embodiment of a device according to one embodiment, in a side view.

FIG. 6a illustrates a schematic cross section of a further embodiment of a device according to one embodiment, in a side view.

FIG. 6b illustrates a schematic view of the electrode of the embodiment in FIG. 6a from the direction of the surrounding volume.

FIG. 6c illustrates a schematic view of the electrode of the embodiment in FIG. 6a from the direction of the inner volume.

FIG. 9 illustrates a schematic cross section of a further embodiment of a device according to one embodiment, in a side view.

DETAILED DESCRIPTION

Figure 1:
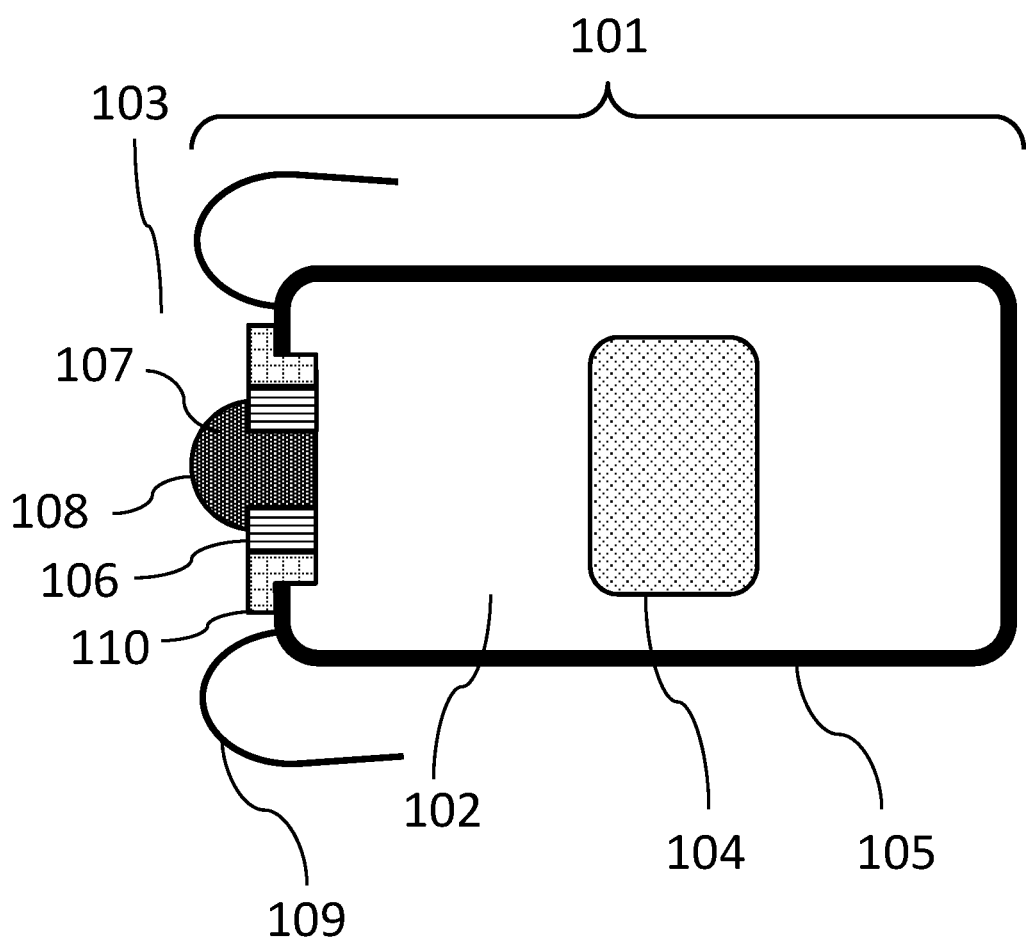
FIG. 1 illustrates a schematic cross section of an embodiment of a device according to one embodiment, in a side view.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

It is generally an object of one embodiment of the present invention to at least partially overcome a disadvantage of the prior art. One object of one embodiment of the invention is to make available a wireless cardiac pacemaker or an implantable biomonitor or both that is less laborious or less expensive or both to produce. Another object of one embodiment of the invention is to make available a method by which a wireless cardiac pacemaker or an implantable biomonitor or both can be produced less laborious or less expensive or both. Another object of one embodiment of the invention is to make available a wireless cardiac pacemaker or an implantable biomonitor or both with increased efficiency. Another object of one embodiment of the invention is to make available a wireless cardiac pacemaker or an implantable biomonitor or both with lower power consumption. Another object of one embodiment of the invention is to make available a wireless cardiac pacemaker or an implantable biomonitor or both with a longer battery life. Another object of one embodiment of the invention is to make available a wireless cardiac pacemaker or an implantable biomonitor or both with increased operational reliability. Another object of one embodiment of the invention is to make available a wireless cardiac pacemaker or an implantable biomonitor or both comprising an electrode array. Another object of one embodiment of the invention is to make available a wireless cardiac pacemaker that permits more positionally precise stimulation. Another object of one embodiment of the invention is to make available a wireless cardiac pacemaker or an implantable biomonitor or both that permits more positionally precise measurement of electrical potentials. Another object of one embodiment of the invention is to make available a wireless cardiac pacemaker with a minimum electrically conductive outer stimulation surface. Another object of one embodiment of the invention is to make available a wireless cardiac pacemaker or an implantable biomonitor or both with a maximum electrode surface. Another object of one embodiment of the invention is to make available a wireless cardiac pacemaker or an implantable biomonitor or both with a plurality of cavities for steroidal anti-inflammatories. Another object of one embodiment of the invention is to make available a wireless cardiac pacemaker or an implantable biomonitor or both which, after implantation in a eukaryotic organism, causes less frequent or less severe or both inflammation. Another object of one embodiment of the invention is to make available a wireless cardiac pacemaker or an implantable biomonitor or both with a reduced number of potential leakage points. Another object of one embodiment of the invention is to make available a wireless cardiac pacemaker or an implantable biomonitor or both with a reduced number of connection points. Another object of one embodiment of the invention is to make available a wireless cardiac pacemaker or an implantable biomonitor or both with an electrode which consists of the smallest possible number of pieces. Another object of one embodiment of the invention is to make available a wireless cardiac pacemaker or an implantable biomonitor or both which is as safe as possible and is hermetically sealed for as long as possible. Another object of one embodiment of the invention is to make available a wireless cardiac pacemaker or an implantable biomonitor or both with an increased operational lifetime. Another object of one embodiment of the invention is to make available a wireless cardiac pacemaker or an implantable biomonitor or both that is less susceptible to interference. Another object of one embodiment of the invention is to make available a method for producing one of the above advantageous wireless cardiac pacemakers or an implantable biomonitor or both. Another object of one embodiment of the invention is to make available an improved wireless cardiac pacemaker or implantable biomonitor or both. Another object of one embodiment of the invention is to make available an improved treatment of bradycardia. Another object of one embodiment of the invention is to make available a more cost-effective treatment of bradycardia. Another object of one embodiment of the invention is to make available a gentler treatment of bradycardia. Another object of one embodiment of the invention is to make available a treatment which involves fewer surgical interventions. Another object of one embodiment of the invention is to make available a lower-risk treatment of bradycardia.

A contribution to the achievement of at least one of the above objects is made by the independent claims. The dependent claims set forth preferred embodiments that contribute to the at least partial achievement of at least one of the objects.

A contribution to the achievement of at least one of the objects according to the invention is made by a device comprising a hollow body, an inner volume and a surrounding volume;
wherein
  a) the inner volume comprises an electronic component;
  b) wherein the hollow body
    i) encloses the inner volume,
    ii) comprises a first component, a second component and an electrode;
  c) the first component is electrically conductive;
  d) the second component electrically insulates the electrode from the first component;
  e) the electrode
    i) comprises a cermet,
    ii) connects the inner volume to the surrounding volume in an electrically conductive manner,
    iii) comprises a contact surface;
  f) the contact surface
    i) is designed for contact with eukaryotic tissue,
    ii) has a maximum distance from the electronic component of less than 80 mm, preferably less than 70 mm, more preferably less than 60 mm, more preferably less than 50 mm, more preferably less than 45 mm, more preferably less than 40 mm, more preferably less than 35 mm, more preferably less than 30 mm, more preferably less than 25 mm, more preferably less than 20 mm, more preferably less than 15 mm, more preferably less than 10 mm, most preferably less than 5 mm.

The electrode preferably connects the inner volume to the surrounding volume in an electrically conductive manner via an ohmic resistance of not more than 10Ω, preferably not more than 1Ω, more preferably not more than 200 mΩ, more preferably not more than 100 mΩ, most preferably not more than 50 mΩ.

In one embodiment according to the invention, the electronic component is an electrical pulse generator.

In one embodiment according to the invention, the electronic component is one chosen from the group consisting of a data memory, a data processing unit, a power source, a recorder, a transmitter, or a combination of at least two thereof. As data memory, any unit for storing data may be chosen that the person skilled in the art deems suitable for the storage of medical data, preferably ECG data, in an implantable appliance. A preferred data memory is a magnetic memory or a flash memory or both. A preferred power source is a battery or an accumulator or both. A preferred recorder is an appliance for recording medical data, preferably heart data, more preferably ECG data. A particularly preferred recorder is a biomonitor. A preferred biomonitor comprises one chosen from the group consisting of an ECG appliance, a Holter monitor, an event recorder, and a loop recorder, or a combination of at least two of these. A preferred ECG appliance is a long-term ECG appliance that preferably stores data generated over a period of at least one hour. A preferred transmitter is designed for wireless and preferably telemetric transmission of data, preferably ECG data. A preferred wireless transmission of data is transmission by waves. Preferred waves are longitudinal waves or transverse waves or both. Preferred longitudinal waves are acoustic waves or sound waves or both. Preferred transverse waves are electromagnetic waves. Preferred electromagnetic waves are waves of the frequency of a mobile radio network or Bluetooth or both. A preferred mobile radio network is a GSM network.

In one embodiment according to the invention, the electrode is designed as a rigid body.

In one embodiment according to the invention, the electrode is formed in one piece. An electrode is in one piece if all the parts belonging to the electrode have been produced as one piece in a production method, without prefabricated parts being joined together. A preferred one-piece electrode does not comprise any solder points or does not comprise any weld points or both.

In one embodiment according to the invention, the cermet comprises a metal to at least 25% by volume, preferably to at least 32% by volume, most preferably to at least 38% by volume, based on the volume of the electrode.

In one embodiment according to the invention, the second component comprises a ceramic.

In one embodiment according to the invention, the hollow body separates the inner volume from the surrounding volume in a hermetically tight manner.

In one embodiment according to the invention, the hollow body comprises a fixing element, said fixing element being designed to fix a position of the hollow body relative to eukaryotic tissue. Here, fixing means that the movement of the hollow body relative to the eukaryotic tissue is limited at least temporarily, preferably permanently. A preferred fixing element is one chosen from the group consisting of a hook, an anchor and a screw, or a combination of at least two thereof. A preferred hollow body comprises more than one fixing element.

In one embodiment according to the invention, the hollow body has a longest extent along a Cartesian spatial direction, wherein the longest extent is less than 150 mm, preferably less than 125 mm, more preferably less than 120 mm, more preferably less than 115 mm, more preferably less than 110 mm, more preferably less than 105 mm, more preferably less than 100 mm, more preferably less than 95 mm, more preferably less than 90 mm, more preferably less than 85 mm, more preferably less than 80 mm, more preferably less than 75 mm, more preferably less than 70 mm, more preferably less than 65 mm, more preferably less than 60 mm, more preferably less than 55 mm, more preferably less than 50 mm, more preferably less than 45 mm, more preferably less than 40 mm, still more preferably less than 35 mm, most preferably less than 30 mm.

A preferred hollow body is elongate. A preferred longest extent of a hollow body along a Cartesian spatial direction is a length of the hollow body.

In one embodiment according to the invention, the hollow body occupies a volume of at most 10 cm$^3$, preferably at most 9 cm$^3$, more preferably at most 8 cm$^3$, more preferably at most 7 cm$^3$, still more preferably at most 6 cm$^3$, most preferably at most 5 cm$^3$.

In this context, the volume occupied by the hollow body is composed of the inner volume and the volumes of all the components of the hollow body. Preferred components of the hollow body are chosen from the group consisting of a housing, at least one electrode, a fixing element, a closure element, a flange, a frame or a combination of at least two of these.

In on embodiment according to the invention, the electrode comprises at least two partial electrodes, wherein each of the partial electrodes
 a) comprises a cermet,
 b) connects the inner volume to the surrounding volume in an electrically conductive manner,
 c) is electrically insulated from the other partial electrode or from the other partial electrodes.

The electrode preferably comprises an array of partial electrodes. Here, an array is a two-dimensional distribution of a plurality of partial electrodes. An array preferably comprises three partial electrodes, more preferably at least four, more preferably at least five, still more preferably at least six, most preferably at least seven partial electrodes.

A preferred partial electrode is formed in one piece. A partial electrode is in one piece if all the parts belonging to the partial electrode have been produced as one piece in a production method, without prefabricated parts being joined together. A preferred one-piece partial electrode does not comprise any solder points or weld points. A further preferred partial electrode is designed as a rigid body. A further preferred partial electrode connects the inner volume to the surrounding volume in an electrically conductive manner via an ohmic resistance of not more than 10Ω, preferably not more than 1Ω, more preferably not more than 200 mΩ, still more preferably not more than 100 mΩ, most preferably not more than 50 mΩ.

In one embodiment according to the invention, the contact surface comprises an electrically conductive partial surface, wherein the electrically conductive partial surface has an outer surface area of less than 25 mm$^2$, preferably less than 15 mm$^2$, more preferably less than 10 mm$^2$, most preferably less than 5 mm$^2$.

In one embodiment according to the invention, the contact surface comprises an electrically conductive partial surface, wherein an inner surface area of the electrically conductive partial surface is at least twice as large as the outer surface area of the electrically conductive partial surface. A preferred inner surface area of a partial surface of the contact surface has been increased in size by etching away a ceramic matrix. Preferably, an inner surface area of a partial surface of the contact surface is as large as possible, so that the electrical capacitance of the electrode is as great as possible. This preferably has the effect that an increased voltage following an electrical pulse drops again after a shorter time. This is preferably advantageous for a measurement of heart activity. A preferred contact surface comprises an electrically conductive partial surface, wherein the electrically conductive partial surface has an inner surface area measuring at least 10 mm$^2$, preferably at least 20 mm$^2$, more preferably at least 30 mm$^2$, most preferably at least 50 mm$^2$.

In one embodiment according to the invention, the contact surface comprises an electrically insulating partial surface, wherein the electrically insulating partial surface has an outer surface area of more than 1 mm$^2$, preferably more than 1.5 mm$^2$, more preferably more than 2 mm$^2$, most preferably more than 5 mm$^2$. An outer surface area of a partial surface of the contact surface is preferably of such a size that the electrode does not perforate eukaryotic tissue.

In one embodiment according to the invention, the contact surface or a partial surface of the contact surface or both has an average roughness Ra in a range of 0.2 to 8 µm, preferably in a range of 0.3 to 8 µm, more preferably in a range of 0.5 to 8 µm, most preferably in a range of 1 to 7 µm.

In one embodiment according to the invention, the contact surface or a partial surface of the contact surface or both has an open pore density in a range of 1,000 to 80,000 ppi, preferably in a range of 2,000 to 60,000 ppi, more preferably in a range of 3,000 to 50,000 ppi, most preferably in a range of 4,000 to 40,000 ppi. An open pore density of the contact surface or of the partial surface of the contact surface or both is preferably increased in size by etching the corresponding surface. In a preferred etching, a ceramic portion of the cermet is etched away, resulting in formation of pores, and a metallic portion of the cermet remains. Preferably, this etching away of the ceramic portion results in a metal foam. The contact surface according to the invention or the partial surface of the contact surface or both can be coated with a biocompatible metal or a biocompatible metal compound or both. A preferred biocompatible metal is iridium. A preferred biocompatible metal compound is a biocompatible metal alloy. Another preferred metal compound is titanium nitride (TiN). An electrical capacitance of the electrode is preferably increased by the aforementioned coating of the contact surface with the metal or the metal compound or both. Preferably, the electrical capacitance is increased to at least 1 $mF/cm^2$, more preferably to at least 2 $mF/cm^2$, more preferably to at least 3 $mF/cm^2$, more preferably to at least 4 $mF/cm^2$, most preferably to at least 5 $mF/cm^2$, based on the surface area of the contact surface. As is mentioned above, the electrical capacitance is preferably increased in order to improve a voltage pulse transfer from the electrode to eukaryotic tissue or to improve detection of an electrical signal from eukaryotic tissue to the electrode or both.

In one embodiment according to the invention, the electrode comprises a hollow space; wherein the hollow space
a) is open toward the surrounding volume, and
b) comprises an active substance.

A preferred active substance is an anti-inflammatory. A preferred anti-inflammatory is chosen from the group consisting of a steroidal anti-inflammatory, a non-steroidal anti-inflammatory and a plant-based anti-inflammatory, or a combination of at least two thereof. A preferred steroidal anti-inflammatory is one chosen from the group consisting of dexamethasone, hydrocortisone and prednisolone, or a combination of at least two thereof. A preferred non-steroidal anti-inflammatory is one chosen from the group consisting of ibuprofen, acetylsalicylic acid, diclofenac, indomethacin and phenylbutazone, or a combination of at least two thereof. A preferred plant-based anti-inflammatory is an ethereal oil. A preferred ethereal oil comprises constituents that have been recovered from a chamomile blossom or arnica blossom or from both. A particularly preferred anti-inflammatory is a steroidal anti-inflammatory. A preferred hollow space open toward the surrounding volume is a bore. A particularly preferred electrode comprises a plurality of hollow spaces, said hollow spaces being open toward the surrounding volume and each containing an active substance.

In one embodiment according to the invention, the hollow body is a therapy appliance. A preferred therapy appliance is implantable. A preferred implantable therapy appliance is implantable in a heart. Another preferred therapy appliance is a defibrillator or a pacemaker or a combination of at least two thereof. Another preferred therapy appliance is an implantable defibrillator or an implantable pacemaker or both. A preferred pacemaker is one chosen from the group consisting of a cardiac pacemaker, a bladder pacemaker, an intestinal pacemaker, a brain pacemaker, a respiratory pacemaker and a diaphragm pacemaker, or a combination of at least two thereof. A particularly preferred pacemaker is a cardiac pacemaker. A preferred cardiac pacemaker is a wireless cardiac pacemaker. Another preferred therapy appliance does not comprise a flexible electrode line, in particular it does not comprise a flexible electrode line between a housing and an electrode. Another preferred therapy appliance is a heart therapy appliance, preferably a cardiac pacemaker, preferably a wireless cardiac pacemaker.

In another embodiment according to the invention, the hollow body is a diagnostic appliance. A preferred diagnostic appliance is implantable. Another preferred diagnostic appliance is a biomonitor. A preferred biomonitor comprises one chosen from the group consisting of an ECG appliance, a Holter monitor, an event recorder, and a loop recorder, or a combination of at least two thereof. A preferred ECG appliance is a long-term ECG appliance that preferably stores data generated over a period of at least one hour. Another preferred diagnostic appliance comprises a transmitter or a data memory or both. A preferred transmitter is designed for wireless and preferably telemetric transmission of data, preferably ECG data. A preferred wireless transmission of data is transmission by waves. Preferred waves are longitudinal waves or transverse waves or both. Preferred longitudinal waves are acoustic waves or sound waves or both. Preferred transverse waves are electromagnetic waves. Preferred electro-magnetic waves are waves of the frequency of a mobile radio network or Bluetooth or both. A preferred mobile radio network is a GSM network. As data memory, any unit for storing data may be chosen that the person skilled in the art deems suitable for the storage of medical data, preferably ECG data, in an implantable appliance. A preferred data memory is a magnetic memory or a flash memory or both.

In one embodiment according to the invention, the first component is a housing; and the first component comprises an attachment flange comprising a flange opening; wherein the flange opening comprises the second component; wherein the second component is a frame comprising a frame opening; wherein the electrode penetrates the frame opening. The attachment flange is preferably fitted into an opening of the housing and welded into place. The frame is preferably fitted into the flange opening and soldered into place. More preferably, the frame and the electrode have been produced in one piece in a sintering process.

In one embodiment according to the invention, the first component is a housing; and the housing comprises a housing opening; wherein the housing opening comprises the second component; wherein the second component is a frame comprising a frame opening; wherein the electrode penetrates the frame opening; wherein the frame comprises a metal content; wherein the metal content of the frame increases radially outward. The frame is preferably fitted into the housing opening and welded in place. More preferably, the frame and the electrode have been produced in one piece in a sintering process. A preferred metal content presents at least two, preferably at least three, more preferably at least four, most preferably at least five jumps along a radius of the frame. Another preferred metal content is a continuous function of a position on a radius of the frame. A preferred metal content comprises a gradient of the metal content in a range of 20 to 80% by weight×$mm^{-1}$, preferably in a range of 25 to 75% by weight×$mm^{-1}$, more preferably in a range of 30 to 70% by weight×$mm^{-1}$, most preferably in a range of 35 to 65% by weight×$mm^{-1}$, along a radius of the frame, in each case based on the total weight of the frame.

A preferred frame comprises a first, a second and a third concentric partial frame, wherein a metal content of the first partial frame is in a range of 0 to 60% by weight, preferably in a range of 10 to 50% by weight, more preferably in a range of 20 to 40% by weight, based on the weight of the first partial frame; wherein a metal content of the second partial frame is in a range of 20 to 80% by weight, preferably in a range of 30 to 70% by weight, more preferably in a range of 40 to 60% by weight based on the weight of the second partial frame; wherein a metal content of the third partial frame is in a range of 40 to 100% by weight, preferably in a range of 50 to 90% by weight, more preferably in a range of 60 to 80% by weight based on the weight of the third partial frame.

The production of a frame according to the invention, comprising a metal content, wherein the metal content of the frame increases radially outward, can be realized as follows. One or more organic films with a low flash point can be arranged concentrically in the housing opening. The films separate various concentric volumes from each other. Powders chosen from the group consisting of a metal powder, a ceramic powder and a cermet powder, or a combination of at least two thereof, can then be introduced into these volumes. The powders are introduced such that the metal content introduced into the various volumes increases from inner volumes toward outer volumes. Separated by the organic films, the materials introduced into the various volumes do not mix during the sintering. Since the organic films have a firing temperature which is below the sintering temperature, the films dissolve during the sintering and diffuse out of the frame. Once the organic films have dissolved, the mutually adjoining materials of the initially separately filled volumes touch each other and in turn establish a cohesive sintered connection.

In one embodiment according to the invention, the second component is a housing. A preferred housing is elongate.

A contribution to achieving at least one of the objects according to the invention is made by a method for producing a device, comprising the method steps of
  a) making available a housing comprising a housing opening;
  b) inserting an electronic component into the housing through the housing opening;
  c) closing the housing opening with a closure element;
  d) connecting the housing to an electrode;
wherein the electrode comprises a cermet, wherein the electrode connects the electronic component to a surrounding of the housing in an electrically conductive manner, wherein the electrode comprises a contact surface, wherein the contact surface is designed for contact with eukaryotic tissue, wherein the contact surface has a maximum distance from the electronic component of less than 80 mm, preferably less than 70 mm, more preferably less than 60 mm, more preferably less than 50 mm, more preferably less than 45 mm, more preferably less than 40 mm, more preferably less than 35 mm, more preferably less than 30 mm, more preferably less than 25 mm, more preferably less than 20 mm, more preferably less than 15 mm, more preferably less than 10 mm, most preferably less than 5 mm. A preferred electronic component is an electronic component in accordance with the above-described device according to the invention. The method preferably comprises a further method step in which an open pore density of the contact surface or of a partial surface of the contact surface or both is increased in size by etching the corresponding surface. In a preferred etching, a ceramic portion of the cermet is etched away, which leads to the formation of pores, and a metallic portion of the cermet remains.

The electrode preferably connects the electronic component to the surrounding of the housing in an electrically conductive manner via an ohmic resistance of not more than $10\Omega$, preferably not more than $1\Omega$, more preferably not more than 200 m$\Omega$, still more preferably not more than 100 m$\Omega$, most preferably not more than 50 m$\Omega$.

A preferred housing is electrically conductive. Another preferred housing comprises a metal. Another preferred housing comprises a biocompatible material. Another preferred housing is elongate. A preferred closure element comprises a biocompatible material. A preferred electronic component moreover comprises one chosen from the group consisting of a control unit, a measuring unit and a battery, or a combination of at least two thereof.

In one embodiment according to the invention, the housing is electrically conductive;
wherein connecting the housing to the electrode comprises the substeps of
  a) connecting the housing to an attachment flange comprising a flange opening;
  b) inserting a frame, which comprises a ceramic and a frame opening, into the flange opening;
wherein the electrode penetrates the frame opening. A preferred connecting of the housing to the attachment flange is a welding. The frame is preferably soldered into the flange opening. More preferably, the frame is soldered into the flange opening with a gold solder. More preferably, the frame and the electrode have been produced in one piece in a sintering process.

In one embodiment according to the invention, the housing is electrically conductive; wherein connecting the housing to the electrode comprises the substep of connecting the housing to a frame comprising a frame opening, a ceramic and a metal content; wherein the electrode penetrates the frame opening; wherein the metal content of the frame increases radially outward. A preferred metal content presents at least two, preferably at least three, more preferably at least four, most preferably at least five jumps along a radius of the frame. Another preferred metal content is a continuous function along a position on a radius of the frame. A preferred metal content comprises a gradient of the metal content in a range of 20 to 80% by weight$\times$mm$^{-1}$, preferably in a range of 25 to 75% by weight$\times$mm$^{-1}$, more preferably in a range of 30 to 70% by weight$\times$mm$^{-1}$, most preferably in a range of 35 to 65% by weight$\times$mm$^{-1}$, along a radius of the frame, in each case based on the total weight of the frame.

A preferred frame comprises a first, a second and a third concentric partial frame, wherein a metal content of the first partial frame is in a range of 0 to 60% by weight, preferably in a range of 10 to 50% by weight, more preferably in a range of 20 to 40% by weight, based on the total weight of the first partial frame; wherein a metal content of the second partial frame is in a range of 20 to 80% by weight, preferably in a range of 30 to 70% by weight, more preferably in a range of 40 to 60% by weight based on the weight of the second partial frame; wherein a metal content of the third partial frame is in a range of 40 to 100% by weight, preferably in a range of 50 to 90% by weight, more preferably in a range of 60 to 80% by weight based on the weight of the third partial frame.

A preferred connecting of the housing to the frame is a welding or a soldering or both. A preferred form of soldering is soldering with a gold solder. More preferably, the frame and the electrode have been produced in one piece in a sintering process.

In one embodiment according to the invention, the housing comprises a ceramic. A preferred housing is electrically insulating.

In one embodiment according to the invention, the closure element is electrically conductive. A preferred closure element comprises a metal. A preferred closure element is hermetically sealed. Another preferred closure element is welded or soldered or both. Another preferred closure element is soldered with a gold solder.

A contribution to achieving at least one of the objects according to the invention is made by a device obtainable by the method according to the invention.

A contribution to achieving at least one of the objects according to the invention is made by a use of an electrode for producing a wireless cardiac pacemaker, wherein the electrode comprises a cermet. A preferred electrode comprises a cermet which comprises a metal to at least 25% by volume, preferably to at least 32% by volume, most preferably to at least 38% by volume, based on the volume of the electrode.

A contribution to achieving at least one of the objects according to the invention is made by a method comprising the method steps of
 a) making available a device according to the invention,
 b) bringing the contact surface into contact with eukaryotic tissue.

In one embodiment according to the invention, a further method step involves introducing the hollow body into an eukaryotic organism. A preferred form of introduction of the hollow body into the eukaryotic organism is implantation.

A contribution to achieving at least one of the objects according to one embodiment of the invention is made by a use of a device according to the invention for a therapy of bradycardia.

First Component

A preferred first component is one chosen from the group consisting of a housing, a closure element, a frame, a plate, or a combination of at least two thereof. A particularly preferred first component is an anode. Another preferred first component comprises a metal. Another preferred first component comprises a biocompatible material.

Second Component

A preferred second component is a frame or a housing or both. Another preferred second component is electrically insulating. Another preferred second component comprises a ceramic. A particularly preferred second component consists of a ceramic.

Frame

According to one embodiment of the invention, a frame is preferably a torus, torus-shaped, or a prism, wherein the prism comprises a first base surface and a second base surface and at least one hollow space, wherein the hollow space comprises a partial surface of the first base surface and a partial surface of the second base surface. The hollow space is designed as a frame opening. A preferred first base surface or a preferred second base surface or both are selected from the group consisting of a circular surface, an elliptical surface, an oval surface, a triangular surface, a square surface, a pentagonal surface, a hexagonal surface, a heptagonal surface, an octagonal surface, a polygonal surface, or a combination of at least two thereof. The partial surface of the first base surface or the partial surface of the second base surface or both comprising the frame opening are preferably chosen from the group consisting of a circular surface, an elliptical surface, an oval surface, a triangular surface, a square surface, a pentagonal surface, a hexagonal surface, a heptagonal surface, an octagonal surface, a polygonal surface, or a combination of at least two thereof. A preferred polygonal surface is a surface of a regular polygon or a surface of an irregular polygon. A very preferred frame is a hollow cylinder or a ring or both. A further preferred frame is a perforated plate. A perforated plate is a plate comprising a plurality of holes that connect opposite surfaces. A radius of the frame is defined for use in this document as follows. If the frame is a torus or torus-shaped, the radius of the frame is the major radius of the torus. If the frame is a prism, the radius of the frame is a straight line which connects an area centroid of a base surface of the prism to a point on the circumference of the base surface. If the frame is a perforated plate, the radius of the frame is a straight line connecting an area centroid of a base surface of the perforated plate to a point on the circumference of the perforated plate.

Contact Surface

A contact surface according to one embodiment of the invention is a surface of the electrode which contacts the surrounding volume. A preferred contact surface is designed to comprise the largest possible outer surface area. A preferred contact surface has a geometric shape with the largest possible outer surface area. Another preferred contact surface bulges out toward the surrounding volume. Another preferred contact surface is sintered.

Electrical Pulse Generator

An electrical pulse generator according to one embodiment of the invention is an electronic circuit or an electronic appliance or both designed to deliver an electrical voltage pulse once or repeatedly for a short period of time. A preferred electrical voltage pulse is a DC pulse. Another preferred voltage pulse has a maximum voltage value of less than 24 V, preferably less than 12 V, more preferably less than 10 V, most preferably less than 2.4 V. A preferred short period of time is shorter than 500 ms, preferably shorter than 100 ms, more preferably shorter than 50 ms, most preferably shorter than 10 ms.

Electrode

A preferred electrode is a cathode or an anode or both. A particularly preferred electrode is a cathode. Another preferred electrode is a tip electrode or a ring electrode or both. A particularly preferred electrode is a tip electrode. A very particularly preferred is a cathode tip. A preferred hollow body according to one embodiment of the invention comprises at least two electrodes, of which at least one is designed according to the invention. Another preferred electrode consists of a cermet.

Metal

All metals familiar to the person skilled in the art may be considered here which, in addition to conductivity, also have good compatibility with eukaryotic tissue. A preferred metal according to one embodiment of the invention is preferably chosen from the group consisting of platinum, iridium, niobium, palladium, iron, stainless steel, cobalt-chromium alloy, molybdenum, tantalum, tungsten, titanium, cobalt and zirconium, or a combination of at least two thereof. A preferred combination is an alloy. A preferred stainless steel is 316L stainless steel. A preferred metal is biocompatible. A preferred alloy is biocompatible.

Cermet

According to one embodiment of the invention, "cermet" is the term used to designate a composite material comprising one or more ceramic materials in at least one metallic matrix or a composite material comprising one or more metallic materials in at least one ceramic matrix or both. To produce a cermet, it is possible for example to use a mixture of at least one ceramic powder and at least one metallic powder, which mixture can, for example, be mixed with at least one binder and, if appropriate, with at least one solvent. The ceramic powder or powders of the cermet preferably have an average grain size of less than 10 µm, preferably less than 5 µm, particularly preferably less than 3 µm. The metallic powder or powders of the cermet preferably have an average grain size of less than 15 µm, preferably less than 10 µm, particularly preferably less than 5 µm. The average grain size is here regarded in particular as the median value or $D_{50}$ value of the grain size distribution. The $D_{50}$ value describes the value at which 50% of the grains of the ceramic powder and/or of the metallic powder are finer than the $D_{50}$ value. A preferred cermet has a high specific conductivity, which is preferably at least 1 S/m, more preferably at least 100 S/m, more preferably at least $10^3$ S/m, more preferably at least $10^4$ S/m, still more preferably at least $10^5$ S/m, and most preferably at least $10^6$ S/m.

The at least one ceramic component of a cermet according to one embodiment of the invention preferably comprises a ceramic according to the invention. The at least one metallic component of a cermet according to the invention preferably comprises one chosen from the group consisting of platinum, iridium, niobium, palladium, iron, stainless steel, cobalt-chromium alloy, molybdenum, tantalum, tungsten, titanium, cobalt and zirconium, or a combination of at least two thereof. A preferred combination is an alloy. A preferred stainless steel is 316L stainless steel. An electrically conductive connection is generally established in the cermet when the metal content is above the so-called percolation threshold at which the metal particles in the sintered cermet are connected to each other at least at points such that electrical conduction is made possible. Depending on the choice of material, experience shows that, for this purpose, the metal content should be at least 25% by volume, preferably at least 32% by volume, most preferably at least 38% by volume, in each case based on the total volume of the cermet.

Ceramic

A ceramic according to one embodiment of the invention can be any ceramic that a person skilled in the art would select for the use according to the invention. The ceramic is preferably chosen from the group consisting of an oxide ceramic, a silicate ceramic, a non-oxide ceramic, or a mixture of at least two thereof.

The oxide ceramic is preferably chosen from the group consisting of a metal oxide, a semimetal oxide or a mixture thereof. The metal of the metal oxide can be chosen from the group consisting of aluminum, beryllium, barium, calcium, magnesium, sodium, potassium, iron, zirconium, titanium, or a mixture of at least two thereof. The metal oxide is preferably chosen from the group consisting of aluminum oxide ($Al_2O_3$), magnesium oxide (MgO), zirconium oxide ($ZrO_2$), yttrium oxide ($Y_2O_3$), aluminum titanate ($Al_2TiO_5$), a piezoelectric ceramic such as lead zirconate ($PbZrO_3$), lead titanate ($PbTiO_3$), and lead zirconate titanate (PZT), or a mixture of at least two thereof. The semi-metal of the semimetal oxide is preferably chosen from the group consisting of boron, silicon, arsenic, tellurium, or a mixture of at least two thereof. Another preferred oxide ceramic comprises one chosen from the group consisting of zirconia-reinforced alumina (ZTA—Zirconia Toughened Aluminum—$Al_2O_3/ZrO_2$), yttrium-reinforced zirconia (Y-TZP), barium (Zr, Ti) oxide, barium (Ce, Ti) oxide, or a combination of at least two thereof.

The silicate ceramic is preferably chosen from the group consisting of a steatite ($Mg_3[Si_4O_{10}(OH)_2]$), cordierite (Mg, $Fe^{2+})_2(Al_2Si)[Al_2Si_4O_{18}]$), mullite ($Al_2Al_{2+2x}Si_{2-2x}O_{10-x}$, with x=oxygen vacancies per unit cell), feldspar (Ba,Ca,Na,K,NH4)(Al,B,Si)$_4O_8$) or a mixture of at least two thereof.

The non-oxide ceramic can be chosen from the group consisting of a carbide, a nitride or a mixture thereof. The carbide can be chosen from the group consisting of silicon carbide (SiC), boron carbide ($B_4C$), titanium carbide (TiC), tungsten carbide, cementite (Fe3C). The nitride can be chosen from the group consisting of silicon nitride ($Si_3N_4$), aluminum nitride (AlN), titanium nitride (TiN), silicon aluminum oxynitride (SIALON), or a mixture of at least two thereof. Another preferred non-oxide ceramic is sodium potassium niobate.

Biocompatible Material

A preferred biocompatible material is one chosen from the group consisting of biotolerant, bioinert and bioactive, or a combination of at least two thereof.

Eukaryotic Tissue

A preferred eukaryotic tissue is animal tissue or human tissue or both.

Distance

According to one embodiment of the invention, a distance between the contact surface and the electronic component is a length of a shortest straight line which connects a point on the contact surface and a point on a surface of the electronic component. A maximum distance between the contact surface and the electronic component is a distance at which the point on the contact surface and the point on a surface of the electronic component were chosen such that the distance becomes a maximum distance.

Electrically Conductive

For use in this document, a body is electrically conductive when an electrical conductivity of the body is at least 0.01 S/m. A body is electrically insulating when the body is not electrically conductive. A surface or partial surface is electrically conductive for use in this document; when a straight prism, which comprises the surface or the partial surface as a base surface, has an identical surface as the second base surface, has a height of 1 m and is made entirely from the material of the surface or partial surface; has an electrical conductivity of at least 0.01 S/m. A surface is electrically insulating when the surface is not electrically conductive.

Inner Surface Area

For use in this document, an inner surface area of a surface is an area content of the surface including all the area contents of all the pores which are open toward the surface.

Outer Surface Area

For use in this document, an outer surface area of a surface is an area content of a partial surface that is visible to the human eye from the outside. In particular, an outer surface area of a surface is an area content of an envelope of the surface, wherein the envelope covers all the open pores of the surface and does not extend into the open pores.

Hermetically Sealed

The hollow body preferably separates the inner volume from the surrounding volume in a hermetically sealed manner. In the context of one embodiment of the invention, the expression "hermetically sealed" can signify that, when the device is used as intended, moisture or gases or both cannot be exchanged, or can be exchanged only minimally, through the hermetically sealed hollow body between the surrounding volume and the inner volume, that is within the customary time intervals (for example 5 to 10 years). One physical parameter which, for example, can describe a permeation of gases or moisture or both through the hollow body is referred to as the leakage rate, which can be determined, for example, by leakage tests. Corresponding leakage tests can be carried out, for example, with helium leak testers and/or mass spectrometers and are specified in the standard Mil-STD-883G Method 1014. The maximum permissible helium leakage rate is defined according to the internal volume of the device to be tested, in this case the inner volume. According to the methods specified in MIL-STD-883G, Method 1014, in paragraph 3.1, and taking into consideration the volumes and cavities of the devices to be tested in the application of one embodiment of the present invention, these maximum permissible helium leakage rates can be, for example, from $1\times10^{-8}$ atm$^x$cm$^3$/s to $1\times10^{-7}$ atm$^x$cm$^3$/s. In the context of one embodiment of the invention, the expression "hermetically sealed" can in particular signify that the hollow body has a helium leakage rate of less than $1\times10^{-7}$ atm$^x$cm$^3$/s. In an advantageous embodiment, the helium leakage rate can be less than $1\times10^{-8}$ atm$^x$cm$^3$/s, in particular less than $1\times10^{-9}$ atm$^x$cm$^3$/s.

For the purpose of standardization, the helium leakage rates mentioned can also be converted to the equivalent standard air leak rate. The definition of the equivalent standard air leak rate and the conversion are specified in standard ISO 3530. Given the nature of use of implantable therapeutic appliances, their hermetic sealing and biocompatibility generally constitute of their most essential requirements. The hollow body proposed here can be placed in particular in the body of a human or animal, in particular of a patient. The hollow body is therefore generally exposed to a fluid from body tissue of the body. It is therefore generally important that body fluid does not penetrate into the hollow body and that fluids do not leak from the hollow body. To ensure this, the hollow body should have an impermeability that is as complete as possible, in particular an impermeability to body fluids.

Attachment Flange

In the present case, it is preferable that the attachment flange is suitable for connecting a ceramic member to an opening of a metallic component. An attachment flange according to one embodiment of the invention preferably comprises only materials chosen from the group consisting of biocompatible, easily processable, corrosion-resistant and permanently and cohesively connectable to the first element and to the second element, or a combination of at least two thereof. A preferred attachment flange comprises one chosen from the group consisting of platinum, iridium, niobium, molybdenum, tantalum, tungsten, titanium, cobalt-chromium alloys, and zirconium, or a combination of at least two thereof. A preferred combination is an alloy.

Sintering

Sintering or a sintering process is understood within the scope of one embodiment of the present invention as generally meaning a method for producing materials or workpieces in which powdered, in particular one chosen from the group consisting of fine-grained substances, ceramic substances and metallic substances or a combination of at least two thereof are heated and thereby bonded. This process can take place without external pressure on the substance to be heated or can in particular take place under increased pressure on the substance to be heated, for example under a pressure of at least 2 bar, preferably higher pressures, for example pressures of at least 10 bar, in particular at least 100 bar or even at least 1000 bar. The process can in particular take place completely or partially at temperatures below the melting temperature of the powdered materials, for example at temperatures of 700° C. to 1400° C. The process can in particular be carried out completely or partially in a tool or a mold or both, so that the sintering process can involve a shaping. Besides the powdered materials, a starting material for the sintering process can comprise further materials, for example one or more binders or one or more solvents, or both. The sintering process can take place in one step or in multiple steps, it being possible for example for the sintering process to be preceded by further steps, for example one or more shaping steps or one or more debinding steps, or both. The sintering or the sintering process thus corresponds to a firing process. The sintering process, in particular for a cermet, can proceed in a way comparable to a sintering process that is usually used for homogeneous powders. For example, the material can be compacted under high temperature and, if appropriate, high pressure in the sintering process, such that the cermet is almost impermeable or has an extremely closed porosity. Cermets are generally distinguished by a particularly high degree of hardness and wear resistance. Compared with sintered hard metals, an electrode containing cermet generally has a higher thermal shock resistance and oxidation resistance and generally has a coefficient of thermal expansion that is adapted to a surrounding insulator.

EMBODIMENTS

Embodiment 1

A device comprising a hollow body, an inner volume and a surrounding volume; wherein
- a) the inner volume comprises an electronic component;
- b) wherein the hollow body
  - i) encloses the inner volume,
  - ii) comprises a first component, a second component and an electrode;
- c) the first component is electrically conductive;
- d) the second component electrically insulates the electrode from the first component;
- e) the electrode
  - i) comprises a cermet,
  - ii) connects the inner volume to the surrounding volume in an electrically conductive manner,
  - iii) comprises a contact surface;
- f) the contact surface
  - i) is designed for contact with eukaryotic tissue,
  - ii) has a maximum distance from the electronic component of less than 80 mm.

Embodiment 2

The device according to embodiment 1, wherein the electronic component is an electrical pulse generator.

Embodiment 3

The device according to embodiment 1, wherein the electronic component is one chosen from the group consisting of a data memory, a data processing unit, a power source, a recorder, a transmitter, or a combination of at least two thereof.

Embodiment 4

The device according to one of the preceding embodiments, wherein the electrode is designed as a rigid body.

Embodiment 5

The device according to one of the preceding embodiments, wherein the electrode is formed in one piece.

Embodiment 6

The device according to one of the preceding embodiments, wherein the cermet comprises a metal to at least 25% by volume based on the volume of the electrode.

Embodiment 7

The device according to one of the preceding embodiments, wherein the second component comprises a ceramic.

Embodiment 8

The device according to one of the preceding embodiments, wherein the hollow body separates the inner volume from the surrounding volume in a hermetically tight manner.

Embodiment 9

The device according to one of the preceding embodiments, wherein the hollow body comprises a fixing element, wherein the fixing element is designed to fix a position of the hollow body relative to eukaryotic tissue.

Embodiment 10

The device according to one of the preceding embodiments, wherein the hollow body has a longest extent along a Cartesian spatial direction, wherein the longest extent is less than 150 mm.

Embodiment 11

The device according to one of the preceding embodiments, wherein the hollow body occupies a volume of at most 10 cm3.

Embodiment 12

The device according to one of the preceding embodiments, wherein the electrode comprises at least two partial electrodes, wherein each of the partial electrodes
a) comprises a cermet,
b) connects the inner volume to the surrounding volume in an electrically conductive manner,
c) is electrically insulated from the other partial electrode or from the other partial electrodes.

Embodiment 13

The device according to one of the preceding embodiments, wherein the contact surface comprises an electrically conductive partial surface, wherein the electrically conductive partial surface has an outer surface area of less than 25 mm2.

Embodiment 14

The device according to one of the preceding embodiments, wherein the contact surface comprises an electrically conductive partial surface, wherein an inner surface area of the electrically conductive partial surface is at least twice as large as the outer surface area of the electrically conductive partial surface.

Embodiment 15

The device according to one of the preceding embodiments, wherein the contact surface comprises an electrically insulating partial surface, wherein the electrically insulating partial surface has an outer surface area of more than 1 mm2.

Embodiment 16

The device according to one of the preceding embodiments, wherein the contact surface or a partial surface of the contact surface or both has an average roughness in a range of 0.2 to 8 μm.

Embodiment 17

The device according to one of the preceding embodiments, wherein the contact surface or a partial surface of the contact surface or both has an open pore density in a range of 1,000 to 80,000 ppi.

Embodiment 18

The device according to one of the preceding embodiments, wherein the electrode comprises a hollow space; wherein the hollow space
a) is open toward the surrounding volume, and
b) comprises an active substance.

Embodiment 19

The device according to one of the preceding embodiments, wherein the hollow body is a therapy appliance.

Embodiment 20

The device according to one of the preceding embodiments, wherein the first component
a) is a housing; and
b) comprises an attachment flange with a flange opening; wherein the flange opening comprises the second component; wherein the second component is a frame comprising a frame opening; wherein the electrode penetrates the frame opening.

Embodiment 21

The device according to any of the embodiments 1 through 19, wherein the first component
a) is a housing; and
b) comprises a housing opening;
wherein the housing opening comprises the second component; wherein the second component is a frame comprising a frame opening; wherein the electrode penetrates the frame opening; wherein the frame comprises a metal content; wherein the metal content of the frame increases radially outward.

Embodiment 22

The device according to any of the embodiments 1 through 19, wherein the second component is a housing.

Embodiment 23

A method for producing a device, comprising the method steps of
a) making available a housing comprising a housing opening;
b) inserting an electronic component into the housing through the housing opening;
c) closing the housing opening with a closure element;
d) connecting the housing to an electrode;

wherein the electrode comprises a cermet, wherein the electrode connects the electronic component to a surrounding of the housing in an electrically conductive manner, wherein the electrode comprises a contact surface, wherein the contact surface is designed for contact with eukaryotic tissue, wherein the contact surface has a maximum distance from the electronic component of less than 80 mm.

Embodiment 24

The method according to embodiment 23, wherein the housing is electrically conductive; wherein connecting the housing to the electrode comprises the substeps of
a) connecting the housing to an attachment flange comprising a flange opening;
b) inserting a frame, which comprises a ceramic and a frame opening, into the flange opening;
wherein the electrode penetrates the frame opening.

Embodiment 25

The method according to embodiment 23, wherein the housing is electrically conductive; wherein connecting the housing to the electrode comprises the substeps of connecting the housing to a frame comprising a frame opening, a ceramic and a metal content; wherein the electrode penetrates the frame opening, wherein the metal content of the frame increases radially outward.

Embodiment 26

The method according to embodiment 23, wherein the housing comprises a ceramic.

Embodiment 27

The method according to any of the embodiments 23 through 26, wherein the closure element is electrically conductive.

Embodiment 28

A device obtainable by the method according to one of embodiments 23 through 27.

Embodiment 29

Use of an electrode for producing a wireless cardiac pacemaker, wherein the electrode comprises a cermet.
Measuring Methods
The following measuring methods were used in the context of one embodiment of the invention. Unless stated otherwise, the measurements were carried out at an ambient temperature of 25° C., an ambient air pressure of 100 kPa (0.986 atm) and a relative humidity of 50%.
Inner Surface Area
Firstly, the outer surface area of the surface is determined as described below. The sample is then positioned in a scanning electron microscope Ultra 55 from Carl Zeiss AG (73447 Oberkochen, Germany) for measuring the surface. The software SmartSEM (likewise from Carl Zeiss AG) is used for imaging purposes. This software is used to select a magnification factor of 500 and an excitation voltage of 20 kV. An image is produced which is completely filled by the surface that is to be measured. The image produced is opened in MS Paint (Microsoft Deutschland GmbH). A square with an edge length of 1 µm is drawn with the aid of the scale. This square is copied 9 times, such that 10 identical squares of edge length 1 µm are obtained. The 10 squares are arranged in two rows, each with 5 squares, starting from the upper left-hand corner of the image. In each square, the number of black surfaces is counted. This number is averaged over the 10 squares. The pore count per 1 µm$^2$ is obtained. The pore count per 1 µm$^2$ is multiplied by the outer surface area in µm$^2$, and the number Z of the pores on the entire surface to be measured is obtained. Moreover, 30 random pores on the image are selected, and their longest extent along a straight line in the plane of the image is determined using the length measurement tool of the SmartSEM software. The average pore diameter d is determined as a mean value across the extents measured on 30 pores. The means pore radius is accordingly r=d/2. The pores are now assumed to be hemispherical on average, and the inner surface area is calculated as:

$$\text{inner surface area} = \text{outer surface area} - (Z \cdot \pi r^2) + (Z \cdot 2\pi r^2) = \text{outer surface area} + Z \cdot \pi r^2.$$

Outer Surface Area
The outer surface area of a surface is determined by a geometrical calculation of the area content of the surface.
Roughness
The roughness is determined, in accordance with EN ISO 4288:1997, as the mean roughness Ra described in the latter.
Electrical Conductivity
The electrical conductivity is measured using a commercially available conductivity meter (GLF 100 Universal-Leitfahigkeitsmessgerat from GHM Messtechnik GmbH, location Greisinger, Regenstauf, Germany).
Open Pore Density
Firstly, a scanning electron microscope image of the surface to be measured is recorded using the Ultra 55 from Carl Zeiss AG (73447 Oberkochen, Germany). The image is generated using the software SmartSEM (likewise from Carl Zeiss AG). This software is used to select a magnification factor of 500 and an excitation voltage of 20 kV. The image produced is opened in MS Paint (Microsoft Deutschland GmbH). Three straight lines are placed across the image. Each straight line begins at a side of the image and ends at the opposite side of the image. For each of the straight lines, the number of pores that the straight line intersects or touches are counted. The length of each straight line is determined by the scale of the image. 1 inch is divided by the length of the straight lines, and the counted number of pores is multiplied by this factor. Thus, for each of the three straight lines, a pore density in ppi is obtained. The average of these three values Is the open pore density to be determined in ppi.
Biocompatibility
The biocompatibility is determined in accordance with the standard 10993-4:2002.
Electrical Capacitance
To measure the electrical capacitance of an electrode, a beaker of sufficient volume is firstly filled with deionized water with 0.9% by weight NaCl based on the solution. Thereafter, a curved stainless steel sheet as counter-electrode is hung over the rim of the beaker, such that the counter-electrode is partially immersed in the water. The beaker is then placed in a heated water bath and set to 37° C. The electrode to be measured is then placed with the side on which the contact surface is located into the solution. The opposite side of the electrode is not immersed in the solution. The experimental set-up is then left for 24 hours. After the 24 hours, a commercially available reference electrode, from Radiometer Analytical (REF621), is immersed in the solution. A potentiostat (Gambry Instrumentation Reference 600) is made available, and the clamps of the potentiostat are attached as follows. The green and blue clamps are shorted and attached to the side of the electrode protruding from the solution. The white clamp is attached to the reference electrode. The orange and the red clamp are shorted and connected to the counter-electrode. The black clamp is used for grounding. Data is recorded using the software Gambry Instrumentation Framework. In this, the desired application is obtained through the tabs Analysis, Electromechanical Impedance and Potentostatic EIS. The following parameters are to be entered: Initial Frequency: 100,000 Hz; Final Frequency: 0.1 Hz; 10 Points; 10 Mv. The measurement is started. A Bode diagram is generated by the software, from which the impedance can be read off at a frequency of 0.1 Hz. The capacitance is calculated as capacitance=1/(impedance·2·π·0.1).

FIG. 1 shows a schematic cross section of an embodiment of a device 100 according to one embodiment of the invention in a side view. The device 100 comprises a hollow body 101, an inner volume 102 and a surrounding volume 103. The hollow body 101 encloses the inner volume 102. The inner volume 102 comprises an electronic component 104, here an electrical pulse generator 104. The hollow body 101 comprises a first component 105, here a housing 105; a second component 106, here a ceramic ring 106; and an electrode 107. The housing 105 is electrically conductive. The housing is made of a biocompatible titanium alloy for medical purposes (available from Hempel Special Metals AG). An attachment flange 110 is welded into a housing opening. The attachment flange 110 is made of a biocompatible titanium alloy for medical purposes (available from Hempel Special Metals AG). A flange opening of the attachment flange 110 comprises the ceramic ring 106. The ceramic ring 106 is soldered into the flange opening with a gold solder. The ceramic ring 106 electrically insulates the housing 105 and the attachment flange 110 from the electrode 107. The ceramic ring is made of $Al_2O_3$. The electrode 107 penetrates a ring opening of the ceramic ring 106. The electrode 107 comprises a cermet. The cermet consists of 45% by weight platinum powder (from Heraeus Precious Metals GmbH & Co. KG) with a grain size $D_{50}$=50 μm, and 45% by weight of aluminum oxide ($Al_2O_3$) (from CeramTech GmbH) with a grain size of $D_{90}$=2 μm, and also 10% by weight of a binder METAWAX P-50 (available from Zschimmer & Schwarz GmbH & Co. KG), based in each case on the total weight of the cermet. The electrode 107 connects the inner volume 102 to the surrounding volume 103 in an electrically conductive manner. The electrode 107 is formed in one piece. The electrode 107 is a rigid body. The electrode 107 comprises a contact surface 108. The contact surface 108 is designed for contact with eukaryotic tissue. The contact surface 108 is designed for contact with human cardiac muscle tissue. The contact surface 108 is directed toward the surrounding volume and bulges out toward the surrounding volume. A maximum distance of the contact surface 108 from the electrical pulse generator 104 is about 50 mm. The electrode 107 and the ceramic ring 106 were produced jointly in one piece in a sintering process. The hollow body 101 moreover comprises a fixing element 109, here a hook 109, on its outer side. The hook 109 is designed to fix a position of the hollow body 101 relative to the human cardiac muscle tissue. The hollow body 101 separates the inner volume 102 from the surrounding volume 103 in a hermetically sealed manner. The hollow body 101 is a wireless cardiac pacemaker 101.

FIG. 2a shows a schematic cross section of a further embodiment of a device 100 according to one embodiment of the invention in a side view. The device 100 comprises a hollow body 101, an inner volume 102 and a surrounding volume 103. The hollow body 101 encloses the inner volume 102. The inner volume 102 comprises an electronic component 104, here an electrical pulse generator 104; a power source 201, here a lithium battery 201; a control unit 202, here a programmable control unit 202; and a measuring unit 203. The hollow body 101 comprises a first component 105, here a housing 105; a second component 106, here a hollow cylinder 106; and an electrode 107. The housing 105 is electrically conductive. The housing is made of a biocompatible titanium alloy for medical purposes (available from Hempel Special Metals AG). The hollow cylinder 106 is welded into a housing opening. The hollow cylinder 106 is made of a ceramic, comprising a metal content, wherein the metal content of the hollow cylinder 106 increases radially outward. The metal content of the hollow cylinder 106 increases radially outward in three steps. The hollow cylinder 106 comprises three concentric partial hollow cylinders 204, 205 and 206. The inner partial hollow cylinder 204 comprises a metal content of 0% by weight based on the total weight of the inner partial hollow cylinder 204. The central partial hollow cylinder 205 comprises a metal content of 40% by weight based on the total weight of the central partial hollow cylinder 205. The outer partial hollow cylinder 206 comprises a metal content of 80% by weight based on the total weight of the outer partial hollow cylinder 206. The metal to which the metal content refers is platinum. The electrode 107 penetrates a hollow cylinder opening of the hollow cylinder 106. The electrode 107 comprises a cermet. The cermet consists of 45% by weight platinum powder (from Heraeus Precious Metals GmbH & Co. KG) with a grain size $D_{50}$=50 μm, and 45% by weight of aluminum oxide ($Al_2O_3$) (from CeramTech GmbH) with a grain size of $D_{90}$=2 μm, and also 10% by weight of a binder METAWAX P-50 (available from Zschimmer & Schwarz GmbH & Co. KG), based in each case on the total weight of the cermet. The electrode 107 connects the inner volume 102 to the surrounding volume 103 in an electrically conductive manner. The electrode 107 is formed in one piece. The electrode 107 is a rigid body. The electrode 107 comprises a contact surface 108. The contact surface 108 is designed for contact with eukaryotic tissue. The contact surface 108 is designed for contact with human cardiac muscle tissue. The contact surface 108 is directed toward the surrounding volume and bulges out toward the surrounding volume. A maximum distance of the contact surface 108 from the electrical pulse generator 104 is about 50 mm. The electrode 107 and the hollow cylinder 106 were produced jointly in one piece in a sintering process. The hollow body 101 moreover comprises a fixing element 109, here a hook 109, on its outer side. The hook 109 is designed to fix a position of the hollow body 101 relative to the human cardiac muscle tissue. The hollow body 101 separates the inner volume 102 from the surrounding volume 103 in a hermetically sealed manner. The hollow body 101 is a wireless cardiac pacemaker 101.

FIG. 2b shows a schematic view of the electrode 107 and of the second component 106 of the embodiment in FIG. 2a from the direction of the surrounding volume 103. The second component 106 is here a hollow cylinder 106. The hollow cylinder 106 is made up of three concentric partial hollow cylinders 204, 205 and 206. The inner partial hollow cylinder 204 comprises a metal content of 0% by weight based on the total weight of the inner partial hollow cylinder 204. The central partial hollow cylinder 205 comprises a metal content of 40% by weight based on the total weight of the central partial hollow cylinder 205. The outer partial hollow cylinder 206 comprises a metal content of 80% by weight based on the total weight of the outer partial hollow cylinder 206.

Figure 3:
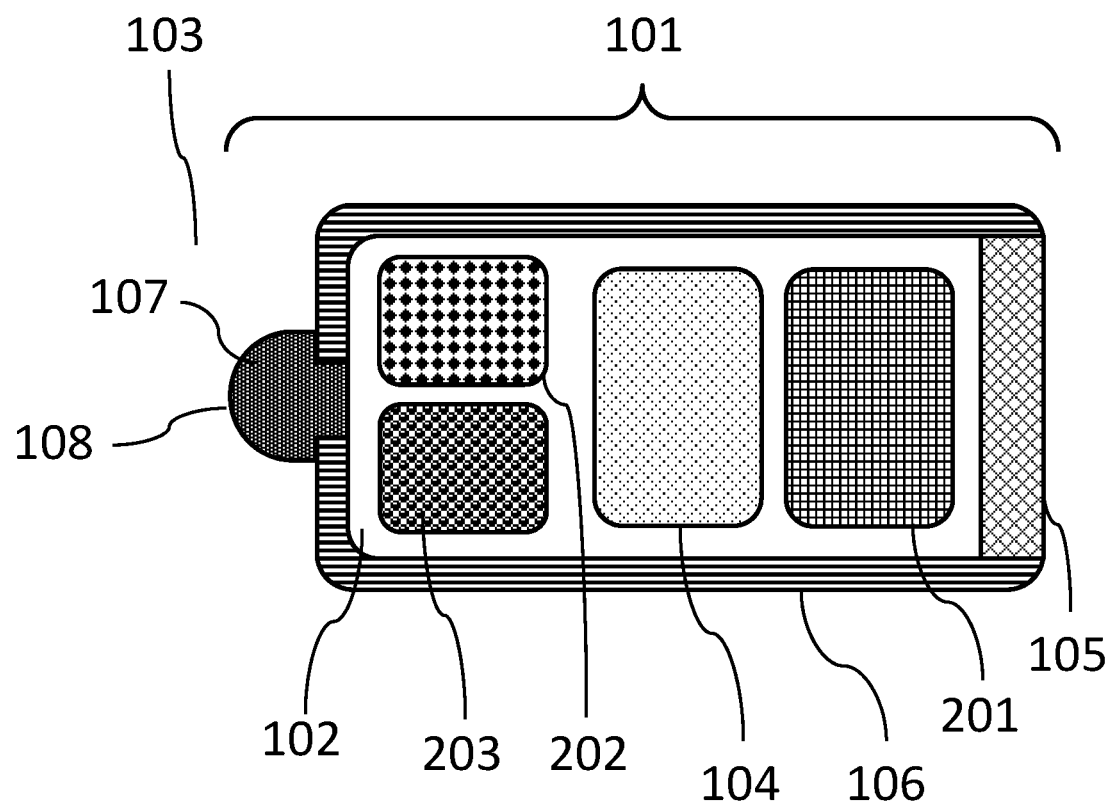
FIG. 3 illustrates a schematic cross section of a further embodiment of a device according to one embodiment, in a side view.

FIG. 3 shows a schematic cross section of a further embodiment of a device 100 according to one embodiment of the invention in a side view. The device 100 comprises a hollow body 101, an inner volume 102 and a surrounding volume 103. The hollow body 101 encloses the inner volume 102. The inner volume 102 comprises an electronic component 104, here an electrical pulse generator 104; a power source 201, here a lithium battery 201; a control unit 202, here a programmable control unit 202; and a measuring unit 203. The hollow body 101 comprises a first component 105, here a closure element 105; a second component 106, here a housing 106; and an electrode 107. The closure element 105 is electrically conductive. The closure element 105 is soldered into the housing 106 with a gold solder. The closure element 105 is made of a biocompatible titanium alloy for medical purposes (available from Hempel Special Metals AG). The housing 106 is electrically insulating. The housing is made of a ceramic. The ceramic comprises $Al_2O_3$. The electrode 107 penetrates a housing opening of the housing 106. The electrode 107 comprises a cermet. The cermet consists of 45% by weight platinum powder (from Heraeus Precious Metals GmbH & Co. KG) with a grain size $D_{50}=50$ µm, and 45% by weight of aluminum oxide ($Al_2O_3$) (from CeramTech GmbH) with a grain size of $D_{90}=2$ µm, and also 10% by weight of a binder METAWAX P-50 (available from Zschimmer & Schwarz GmbH & Co. KG), based in each case on the total weight of the cermet. The electrode 107 connects the inner volume 102 to the surrounding volume 103 in an electrically conductive manner. The electrode 107 is formed in one piece. The electrode 107 is a rigid body. The electrode 107 comprises a contact surface 108. The contact surface 108 is designed for contact with eukaryotic tissue. The contact surface 108 is designed for contact with human cardiac muscle tissue. The contact surface 108 is directed toward the surrounding volume and bulges out toward the surrounding volume. A maximum distance of the contact surface 108 from the electrical pulse generator 104 is about 50 mm. The electrode 107 and the housing 106 were produced jointly in one piece in a sintering process. The hollow body 101 separates the inner volume 102 from the surrounding volume 103 in a hermetically sealed manner. The hollow body 101 is a wireless cardiac pacemaker 101.

Figure 4:
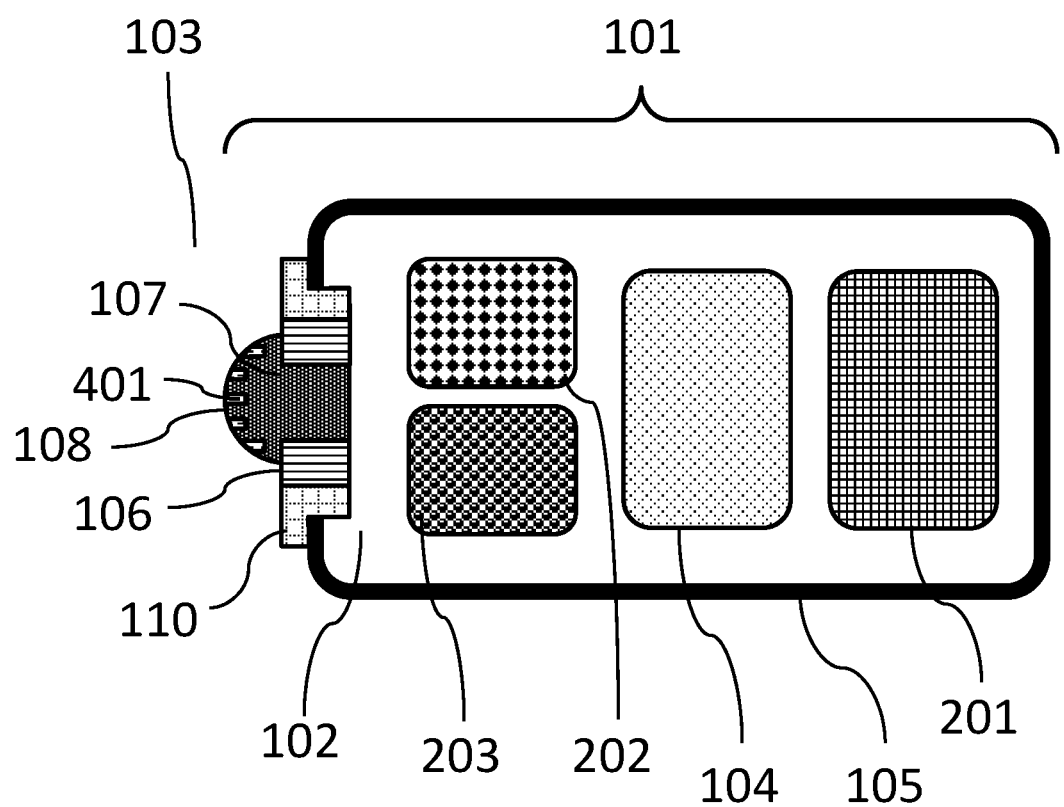
FIG. 4 illustrates a schematic cross section of a further embodiment of a device according to one embodiment, in a side view.

FIG. 4 shows a schematic cross section of a further embodiment of a device 100 according to one embodiment of the invention in a side view. The device 100 comprises a hollow body 101, an inner volume 102 and a surrounding volume 103. The hollow body 101 encloses the inner volume 102. The inner volume 102 comprises an electronic component 104, here an electrical pulse generator 104; a power supply 201, here a lithium battery 201; a control unit 202, here a programmable control unit 202; and a measuring unit 203. The hollow body 101 comprises a first component 105, here a housing 105; a second component 106, here a ceramic ring 106; and an electrode 107. The housing 105 is electrically conductive. The housing is made of a biocompatible titanium alloy for medical purposes (available from Hempel Special Metals AG). An attachment flange 110 is welded into a housing opening. The attachment flange 110 is made of a biocompatible titanium alloy for medical purposes (available from Hempel Special Metals AG). A flange opening of the attachment flange 110 comprises the ceramic ring 106. The ceramic ring 106 is soldered into the flange opening with a gold solder. The ceramic ring 106 electrically insulates the housing 105 and the attachment flange 110 from the electrode 107. The ceramic ring 106 is made of $Al_2O_3$. The electrode 107 penetrates a ring opening of the ceramic ring 106. The electrode 107 comprises a cermet. The cermet consists of 45% by weight platinum powder (from Heraeus Precious Metals GmbH & Co. KG) with a grain size $D_{50}=50$ µm, and 45% by weight of aluminum oxide ($Al_2O_3$) (from CeramTech GmbH) with a grain size of $D_{90}=2$ µm, and also 10% by weight of a binder METAWAX P-50 (available from Zschimmer & Schwarz GmbH & Co. KG), based in each case on the total weight of the cermet. The electrode 107 connects the inner volume 102 to the surrounding volume 103 in an electrically conductive manner. The electrode 107 is formed in one piece. The electrode 107 is a rigid body. The electrode 107 comprises a contact surface 108. The contact surface 108 is designed for contact with eukaryotic tissue. The contact surface 108 is designed for contact human cardiac muscle tissue. The contact surface 108 is directed toward the surrounding volume and bulges out toward the surrounding volume. A maximum distance of the contact surface 108 from the electrical pulse generator 104 is about 50 mm. The electrode 107 and the ceramic ring 106 were produced jointly in one piece in a sintering process. The electrode 107 comprises a plurality of hollow spaces 401, which are open toward the surrounding volume 103. The hollow spaces 401 are bores 401. The bores 401 are distributed on the contact surface 108. Each of the bores 401 comprises a medicament containing a steroidal anti-inflammatory. The hollow body 101 separates the inner volume 102 from the surrounding volume 103 in a hermetically sealed manner. The hollow body 101 is a wireless cardiac pacemaker 101.

FIG. 5 shows a schematic cross section of a further embodiment of a device 100 according to one embodiment of the invention in a side view. The device 100 comprises a hollow body 101, an inner volume 102 and a surrounding volume 103. The hollow body 101 encloses the inner volume 102. The inner volume 102 comprises an electronic component 104, here an electrical pulse generator 104; a power supply 201, here a lithium battery 201; a control unit 202, here a programmable control unit 202; and a measuring unit 203. The hollow body 101 comprises a first component 105, here a housing 105; a second component 106, here a ceramic ring 106; and an electrode 107. The housing 105 is electrically conductive. The housing is made of a biocompatible titanium alloy for medical purposes (available from Hempel Special Metals AG). An attachment flange 110 is welded into a housing opening. The attachment flange 110 is made of a biocompatible titanium alloy for medical purposes (available from Hempel Special Metals AG). A flange opening of the attachment flange 110 comprises the ceramic ring 106. The ceramic ring 106 is soldered into the flange opening with a gold solder. The ceramic ring 106 electrically insulates the housing 105 and the attachment flange 110 from the electrode 107. The ceramic ring 106 is made of $Al_2O_3$. The electrode 107 penetrates a ring opening of the ceramic ring 106. The electrode 107 comprises a cermet. The cermet consists of 45% by weight platinum powder (from Heraeus Precious Metals GmbH & Co. KG) with a grain size $D_{50}=50$ µm, and 45% by weight of aluminum oxide ($Al_2O_3$) (from CeramTech GmbH) with a grain size of $D_{90}=2$ µm, and also 10% by weight of a binder METAWAX P-50 (available from Zschimmer & Schwarz GmbH & Co. KG), based in each case on the total weight of the cermet.

The electrode 107 connects the inner volume 102 to the surrounding volume 103 in an electrically conductive manner. The electrode 107 is formed in one piece. The electrode 107 is a rigid body. The electrode 107 comprises a contact surface 108. The contact surface 108 is designed for contact with eukaryotic tissue. The contact surface 108 is designed for contact with human cardiac muscle tissue. The contact surface 108 is directed toward the surrounding volume and bulges out toward the surrounding volume. A maximum distance of the contact surface 108 from the electrical pulse generator 104 is about 50 mm. The electrode 107 and the ceramic ring 106 were produced jointly in one piece in a sintering process. The contact surface 108 comprises electrically conductive partial surfaces 501 and electrically insulating partial surfaces 502. The inner surface area of all the electrically conductive partial surfaces 501 measures 25 mm². The outer surface area of all the electrically conductive partial surfaces 501 measures 5 mm². The outer surface area of all the electrically insulating partial surfaces 502 measures 20 mm². The overall outer surface area of the contact surface 108 is so great that the electrode 107 does not perforate the cardiac muscle tissue. The hollow body 101 separates the inner volume 102 from the surrounding volume 103 in a hermetically sealed manner. The hollow body 101 is a wireless cardiac pacemaker 101.

FIG. 6a shows a schematic cross section of a further embodiment of a device 100 according to one embodiment of the invention in a side view. The device 100 comprises a hollow body 101, an inner volume 102 and a surrounding volume 103. The hollow body 101 encloses the inner volume 102. The inner volume 102 comprises an electronic component 104, here an electrical pulse generator 104; a power supply 201, here a lithium battery 201; a control unit 202, here a programmable control unit 202; and a measuring unit 203. The hollow body 101 comprises a first component 105, here a housing 105; a second component 106, here a ceramic ring 106; and an electrode 107. The housing 105 is electrically conductive. The housing is made of a biocompatible titanium alloy for medical purposes (available from Hempel Special Metals AG). An attachment flange 110 is welded into a housing opening. The attachment flange 110 is made of a biocompatible titanium alloy for medical purposes (available from Hempel Special Metals AG). A flange opening of the attachment flange 110 comprises the ceramic ring 106. The ceramic ring 106 is soldered into the flange opening with a gold solder. The ceramic ring 106 electrically insulates the housing 105 and the attachment flange 110 from the electrode 107. The ceramic ring 106 is made of $Al_2O_3$. The electrode 107 penetrates a ring opening of the ceramic ring 106. The electrode 107 comprises a cermet. The cermet consists of 45% by weight platinum powder (from Heraeus Precious Metals GmbH & Co. KG) with a grain size $D_{50}=50$ µm, and 45% by weight of aluminum oxide ($Al_2O_3$) (from CeramTech GmbH) with a grain size of $D_{90}=2$ µm, and also 10% by weight of a binder METAWAX P-50 (available from Zschimmer & Schwarz GmbH & Co. KG), based in each case on the total weight of the cermet. The electrode 107 connects the inner volume 102 to the surrounding volume 103 in an electrically conductive manner. The electrode comprises a contact surface 108. The contact surface 108 is designed for contact with eukaryotic tissue. The contact surface 108 is designed for contact with human cardiac muscle tissue. The contact surface 108 is directed toward the surrounding volume and bulges out toward the surrounding volume. A maximum distance of the contact surface 108 from the electrical pulse generator 104 is about 50 mm. The electrode 107 and the ceramic ring 106 were produced jointly in one piece in a sintering process. The electrode 107 comprises four partial electrodes 601. Each of the partial electrodes 601 connects the inner volume 102 to the surrounding volume 103 in an electrically conductive manner. Each partial electrode 601 is electrically insulated from the other partial electrodes 601 by a ceramic 602. Each of the partial electrodes 601 is formed in one piece. Each of the partial electrodes 601 is a rigid body. The hollow body 101 separates the inner volume 102 from the surrounding volume 103 in a hermetically sealed manner. The hollow body 101 is a wireless cardiac pacemaker 101.

FIG. 6b shows a schematic view of the electrode 107 of the embodiment in FIG. 6a from the direction of the surrounding volume 103. The figure also shows the ceramic ring 106 and the attachment flange 110, and also the ceramic 602 which electrically insulates the partial electrodes 601 from each other.

FIG. 6c shows a schematic view of the electrode 107 of the embodiment in FIG. 6a from the direction of the inner volume 102. The figure also shows the ceramic ring 106 and the attachment flange 110, and also the ceramic 602 which electrically insulates the partial electrodes 601 from each other.

Figure 7A:
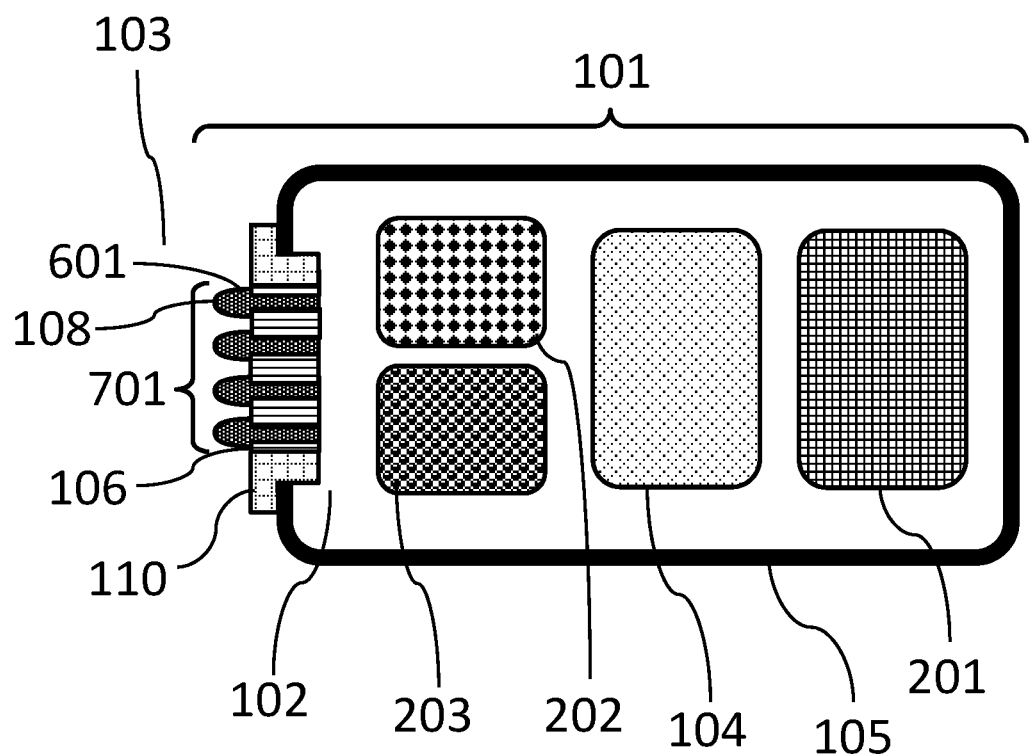
FIG. 7a illustrates a schematic cross section of a further embodiment of a device according to one embodiment, in a side view.

FIG. 7a shows a schematic cross section of a further embodiment of a device 100 according to one embodiment of the invention in a side view. The device 100 comprises a hollow body 101, an inner volume 102 and a surrounding volume 103. The hollow body 101 encloses the inner volume 102. The inner volume 102 comprises an electronic component 104, here an electrical pulse generator 104; a power supply 201, here a lithium battery 201; a control unit 202, here a programmable control unit 202; and a measuring unit 203. The hollow body 101 comprises a first component 105, here a housing 105; a second component 106, here a perforated plate 106; and an electrode 107, wherein the electrode 107 is composed of a plurality of partial electrodes 601. The housing 105 is electrically conductive. The housing is made of a biocompatible titanium alloy for medical purposes (available from Hempel Special Metals AG). An attachment flange 110 is welded into a housing opening. The attachment flange 110 is made of a biocompatible titanium alloy for medical purposes (available from Hempel Special Metals AG). A flange opening of the attachment flange 110 comprises the perforated plate 106. The perforated plate 106 is soldered into the flange opening with a gold solder. The perforated plate 106 electrically insulates the housing 105 and the attachment flange 110 from the electrode 107. The perforated plate 106 is made of $Al_2O_3$. Each partial electrode 601 penetrates a respective hole of the perforated plate 106. The partial electrodes 601 and thus the electrode 107 comprise a cermet. The cermet consists of 45% by weight platinum powder (from Heraeus Precious Metals GmbH & Co. KG) with a grain size $D_{50}=50$ µm, and 45% by weight of aluminum oxide ($Al_2O_3$) (from CeramTech GmbH) with a grain size of $D_{90}=2$ µm, and also 10% by weight of a binder METAWAX P-50 (available from Zschimmer & Schwarz GmbH & Co. KG), based in each case on the total weight of the cermet. Each of the partial electrodes 601 connects the inner volume 102 to the surrounding volume 103 in an electrically conductive manner. Each partial electrode 601 is electrically insulated from the other partial electrodes 601 by the perforated plate 106. Each of the partial electrodes 601 is formed in one piece. Each of the partial electrodes 601 is a rigid body. The partial electrodes 601 form an array of partial electrodes 701. The electrode 107 comprises a contact surface 108. The contact surface 108 is designed for contact with eukaryotic tissue. The contact surface 108 is designed for contact with human cardiac muscle tissue. The contact surface 108 is directed toward the surrounding volume and bulges out toward the surrounding volume. A maximum distance of the contact surface 108 from the electrical pulse generator 104 is about 50 mm. The electrode 107 and the perforated plate 106 were produced jointly in one piece in a sintering process. The hollow body 101 separates the inner volume 102 from the surrounding volume 103 in a hermetically sealed manner. The hollow body 101 is a wireless cardiac pacemaker 101.

Figure 7B:
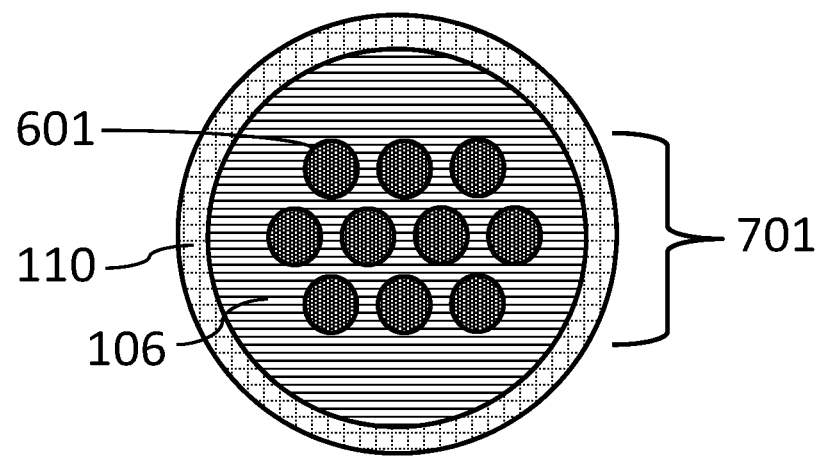
FIG. 7b illustrates a schematic view of the electrode of the embodiment in FIG. 7a from the direction of the surrounding volume.

FIG. 7b shows a schematic view of the electrode 107 of the embodiment in FIG. 7a from the direction of the surrounding volume 103. The figure also shows the perforated plate 106, which electrically insulates the partial electrodes 601 from each other, and the attachment flange 110.

Figure 8:
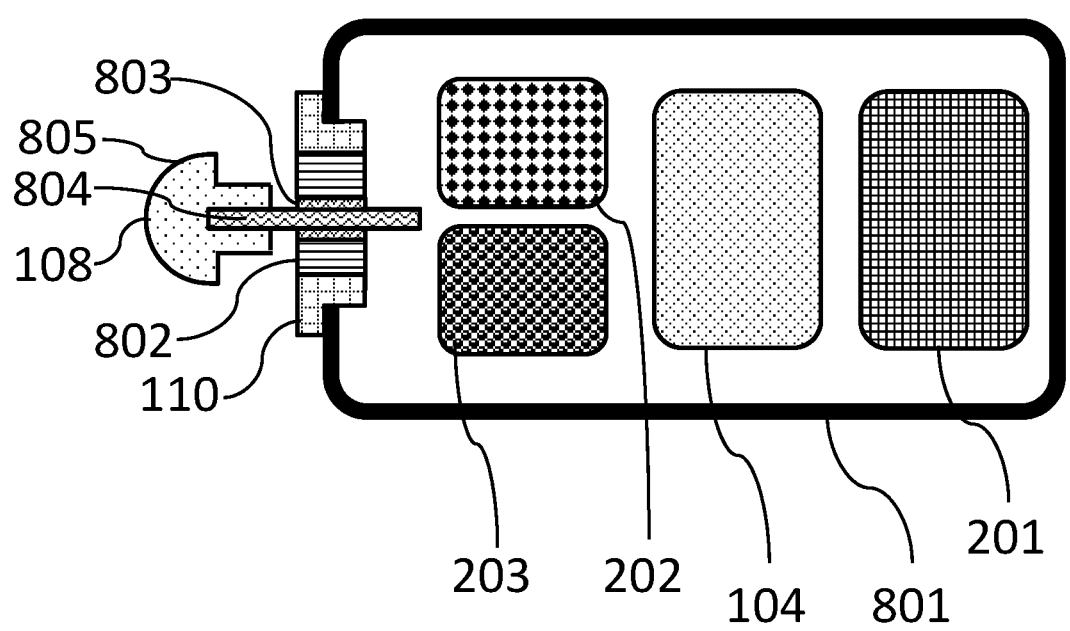
FIG. 8 illustrates a schematic cross section of a wireless cardiac pacemaker not according to one embodiment, in a side view.

FIG. 8 shows a schematic cross section of a wireless cardiac pacemaker 800 not according to one embodiment of the invention, in a side view. The wireless cardiac pacemaker 800 comprises a housing 801 which encloses a power supply 201, here a battery 201; an electronic component 104, here an electrical pulse generator 104; a control unit 202; and a measuring unit 203. An attachment flange 110 is welded into a housing opening of the housing 801. A ceramic ring 802 is soldered into a flange opening of the attachment flange 110 with a gold solder. A feed-through wire 804 is soldered into a ring opening of the ceramic ring 802 with a gold solder 803. A contact body 805 is welded onto an end of the feed-through wire 804 lying outside the housing 801. The contact body 805 comprises a contact surface 108. The contact surface 108 is designed for contact with eukaryotic tissue. The contact surface 108 is designed for contact with human cardiac muscle tissue. The contact surface 108 is directed toward the surrounding volume and bulges out toward the surrounding volume. A maximum distance of the contact surface 108 from the electrical pulse generator 104 is about 50 mm. The feed-through wire 804 and the contact body 805 together form an electrode not according to one embodiment of the invention. The electrode not according to one embodiment of the invention is made of a platinum-iridium alloy. The electrode not according to one embodiment of the invention is designed as a rigid body and is composed of several pieces.

FIG. 9 shows a schematic cross section of a further embodiment of a device 100 according to one embodiment of the invention in a side view. The device 100 comprises a hollow body 101, an inner volume 102 and a surrounding volume 103. The hollow body 101 encloses the inner volume 102. The inner volume 102 comprises an electronic component 104, here an ECG unit 104. The hollow body 101 comprises a first component 105, here a housing 105; a second component 106, here a ceramic ring 106; and an electrode 107. The housing 105 is electrically conductive. The housing is made of a biocompatible titanium alloy for medical purposes (available from Hempel Special Metals AG). An attachment flange 110 is welded into a housing opening. The attachment flange 110 is made of a biocompatible titanium alloy for medical purposes (available from Hempel Special Metals AG). A flange opening of the attachment flange 110 comprises the ceramic ring 106. The ceramic ring 106 is soldered into the flange opening with a gold solder. The ceramic ring 106 electrically insulates the housing 105 and the attachment flange 110 from the electrode 107. The ceramic ring 106 is made of $Al_2O_3$. The electrode 107 penetrates a ring opening of the ceramic ring 106. The electrode 107 comprises a cermet. The cermet consists of 45% by weight platinum powder (from Heraeus Precious Metals GmbH & Co. KG) with a grain size $D_{50}$=50 μm, and 45% by weight of aluminum oxide ($Al_2O_3$) (from CeramTech GmbH) with a grain size of $D_{90}$=2 μm, and also 10% by weight of a binder METAWAX P-50 (available from Zschimmer & Schwarz GmbH & Co. KG), based in each case on the total weight of the cermet. The electrode 107 connects the inner volume 102 to the surrounding volume 103 in an electrically conductive manner. The electrode 107 is formed in one piece. The electrode 107 is a rigid body. The electrode comprises a contact surface 108. The contact surface 108 is designed for contact with eukaryotic tissue. The contact surface 108 is directed toward the surrounding volume and bulges out toward the surrounding volume. A maximum distance of the contact surface 108 from the ECG unit 104 is about 50 mm. The electrode 107 and the ceramic ring 106 were produced jointly in one piece in a sintering process. The hollow body 101 separates the inner volume 102 from the surrounding volume 103 in a hermetically sealed manner. The hollow body 101 is an implantable biomonitor 101.

LIST OF REFERENCE SIGNS

- 100 device according to the invention
- 101 hollow body
- 102 inner volume
- 103 surrounding volume
- 104 electronic component
- 105 first component
- 106 second component
- 107 electrode
- 108 contact surface
- 109 fixing element
- 110 attachment flange
- 201 power supply
- 202 control unit
- 203 measuring unit
- 204 inner partial hollow cylinder
- 205 central partial hollow cylinder
- 206 outer partial hollow cylinder
- 401 hollow space
- 501 electrically conductive partial surface
- 502 electrically insulating partial surface
- 601 partial electrode
- 602 ceramic
- 701 array of partial electrodes
- 800 wireless cardiac pacemaker not according to the invention
- 801 housing
- 802 ceramic ring
- 803 gold solder
- 804 feed-through wire
- 805 contact body

The invention claimed is:

1. A device comprising a hollow body, an inner volume and a surrounding volume;
   wherein
   a) the inner volume comprises an electronic component;
   b) wherein the hollow body
      i) encloses the inner volume,
      ii) comprises a first component, a second component and an electrode;
   c) the first component is electrically conductive;
   d) the second component electrically insulates the electrode from the first component;

e) the electrode
   i) comprises a cermet,
   ii) connects the inner volume to the surrounding volume in an electrically conductive manner,
   iii) comprises a contact surface;
f) the contact surface
   i) is designed for contact with eukaryotic tissue,
   ii) has a maximum distance from the electronic component of less than 80 mm and
A) the first component is a housing, and the first component comprises an attachment flange comprising a flange opening, wherein the flange opening comprises the second component, wherein the second component is a frame comprising a frame opening, wherein the electrode penetrates the frame opening, wherein the frame and the electrode are sintered such that they are one piece; or
B) the second component is a housing, wherein the electrode and the housing are sintered such that they are one piece.

2. The device of claim 1, wherein the electronic component is an electrical pulse generator.

3. The device of claim 1, wherein the electrode is designed as a rigid body.

4. The device of claim 1, wherein the second component comprises a ceramic.

5. The device of claim 1, wherein the contact surface comprises an electrically conductive partial surface, wherein the electrically conductive partial surface has an outer surface area of less than 25 mm$^2$.

6. The device of claim 1, wherein the contact surface comprises an electrically conductive partial surface, wherein an inner surface area of the electrically conductive partial surface is at least twice as large as the outer surface area of the electrically conductive partial surface.

7. The device of claim 1, wherein the contact surface or a partial surface of the contact surface or both has an average roughness in a range of 0.2 to 8 μm.

8. The device of claim 1, wherein the contact surface or a partial surface of the contact surface or both has an open pore density in a range of 1,000 to 80,000 ppi.

9. The device of claim 1, wherein the hollow body is a therapy appliance.

10. A device comprising:
an inner volume comprising an electronic component;
a hollow body enclosing the inner volume and comprising a first component, a second component, and an electrode; and
a surrounding volume;
wherein the first component is electrically conductive and the second component electrically insulates the electrode from the first component;
wherein the electrode comprises a contact surface, comprises a cermet, and connects the inner volume to the surrounding volume in an electrically conductive manner;
wherein the contact surface is configured for contacts with eukaryotic tissue and has a maximum distance from the electronic component of less than 80 mm; and
wherein the contact surface or a partial surface of the contact surface or both has an average roughness in a range of 0.2 to 8 μm, or an open pore density in a range of 1,000 to 80,000 ppi.

11. A method for producing a device, comprising:
providing a housing comprising a housing opening;
inserting an electronic component into the housing through the housing opening;
closing the housing opening with a closure element; and
connecting the housing to an electrode;
wherein the electrode comprises a cermet;
wherein the electrode connects the electronic component to a surrounding of the housing in an electrically conductive manner;
wherein the electrode comprises a contact surface;
wherein the contact surface is designed for contact with eukaryotic tissue;
wherein the contact surface has a maximum distance from the electronic component of less than 80 mm; and
wherein
A) the housing is electrically conductive, wherein connecting the housing to the electrode comprises connecting the housing to an attachment flange comprising a flange opening, and inserting a frame, which comprises a ceramic and a frame opening, into the flange opening, wherein the electrode penetrates the frame opening, and wherein the frame and the electrode are sintered such that they are one piece; or
B) the closure element is electrically conductive and the housing comprises a ceramic, and wherein the electrode and the housing are sintered such that they are one piece.

12. The method of claim 11, wherein the housing is electrically conductive, wherein connecting the housing to the electrode comprises connecting the housing to a frame comprising a frame opening, a ceramic and a metal content, wherein the electrode penetrates the frame opening, and wherein the metal content of the frame increases radially outward.

13. A device obtained by the method of claim 11.

14. Use of the device of claim 1 for a therapy of bradycardia.

15. A method for producing a device, the method comprising:
providing a housing comprising a housing opening;
inserting an electronic component into the housing through the housing opening;
closing the housing opening with a closure element and connecting the housing to an electrode;
wherein the electrode comprises a cermet;
wherein the electrode connects the electronic component to a surrounding of the housing in an electrically conductive manner;
wherein the electrode comprises a contact surface;
wherein the contact surface is designed for contact with eukaryotic tissue;
wherein the contact surface has a maximum distance from the electronic component of less than 80 mm; and
wherein the contact surface or a partial surface of the contact surface or both has
an average roughness in a range of 0.2 to 8 μm or,
an open pore density in a range of 1,000 to 80,000 ppi.

* * * * *